US006992188B1

(12) United States Patent
Chen

(10) Patent No.: US 6,992,188 B1
(45) Date of Patent: *Jan. 31, 2006

(54) SUBSTITUTED HETEROCYCLIC DERIVATIVES

(75) Inventor: Yuhpyng L. Chen, Waterford, CT (US)

(73) Assignee: Pfizer, Inc., New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/764,110

(22) Filed: Dec. 6, 1996

Related U.S. Application Data

(60) Provisional application No. 60/008,396, filed on Dec. 8, 1995.

(51) Int. Cl.
  C07D 487/04 (2006.01)
  C07D 471/04 (2006.01)
  A61K 31/522 (2006.01)
  A61K 31/519 (2006.01)
  A61P 19/02 (2006.01)

(52) U.S. Cl. ................. 544/280; 544/262; 544/263; 544/276; 544/278; 544/350; 546/114; 546/115; 546/117; 546/118; 546/119; 546/121

(58) Field of Classification Search ............. 544/280; 514/258
  See application file for complete search history.

(56) References Cited

U.S. PATENT DOCUMENTS

| 4,605,642 A | 8/1986 | Rivier et al. ................ 514/12 |
| 4,725,601 A | 2/1988 | Ueda et al. ................. 514/300 |
| 4,904,666 A | 2/1990 | Friebe et al. ............... 514/258 |
| 5,028,605 A | 7/1991 | Sablayrolles et al. .... 514/228.5 |
| 5,063,245 A | 11/1991 | Abreu et al. ............... 514/404 |
| 5,223,540 A | 6/1993 | Wurtman et al. ........... 514/640 |
| 5,464,872 A | 11/1995 | Langlois et al. ........... 514/630 |
| 5,541,054 A | 7/1996 | Miller et al. ............... 430/572 |
| 5,561,134 A | 10/1996 | Spada et al. ............... 514/266 |
| 5,597,826 A | 1/1997 | Howard et al. ............. 514/255 |
| 5,710,168 A | 1/1998 | Chenard .................... 514/327 |
| 5,744,501 A | 4/1998 | Norden ...................... 514/614 |
| 5,776,969 A | 7/1998 | James ........................ 514/418 |
| 5,795,895 A | 8/1998 | Anchors ..................... 514/253 |
| 5,852,031 A | 12/1998 | Desai et al. ................ 514/279 |
| 6,552,192 B1 * | 4/2003 | Hanus et al. ............... 544/280 |
| 2005/0038049 A1 * | 2/2005 | Ding et al. ............. 514/265.1 |
| 2005/0107343 A1 * | 5/2005 | Kasibhatia et al. .......... 514/81 |

FOREIGN PATENT DOCUMENTS

| EP | 0157637 | 10/1985 |
| WO | WO9413676 | 6/1994 |
| WO | WO9413677 | 6/1994 |
| WO | WO9533750 | 12/1995 |
| WO | WO9534563 | 12/1995 |
| WO | WO9911643 | 3/1999 |

OTHER PUBLICATIONS

Bisagni, J Org Chem 47, 1500.*
Jorgensen, Chem Abs 102, 78815 (1984).*
Traxler, J Med Chem 39, 2285 (1996).*
Chalmers, TiPS 17(4), 166, 1996.*
Stratakis, Endocrinology: Basic and Clinical Principles (Humana Press, Totowa NJ), p185-209, 1997.*
DeVita, ed, "Cancer: Principles & Practices of Oncology, 5th Edition", index pp. 24-25, 1997.*
Peckam, ed., Oxford Textbook of Oncology, vol. 1, p. 452, 1995.*
Foster, "Syndrome of Inapproproiate Antidiuretic Hormone" http://www.emedicine.com/emerg/topic784.htm, 1997.*
The American Heritage College Dictionary (Houghton Mifflin Company USA; 1993), p. 1105 and p. 399.
Physicians's Desk Reference 52ed (Medical Economics Company, Inc., USA, 1998) pp. 472-474.
REVIA (naltrexone HCI), pp. 1-15, Dupont Pharma 1995 (www.dupontmerk.com).
Owens, M.J., and Nerneroff, C.B., Pharm. Rev., vol. 43, No. 4, 425-473 (1991).
Strijbos, P.J.L.M., et al., Brain Res. 656, pp. 405-408 (1994).
Lyons, M.K., et al., Brain Res. 545, pp. 339-342 (1991).

(Continued)

Primary Examiner—Mark L. Berch
(74) Attorney, Agent, or Firm—Ladas & Parry LLP

(57) ABSTRACT

Corticotropin-releasing factor (CRF) antagonists having the formula

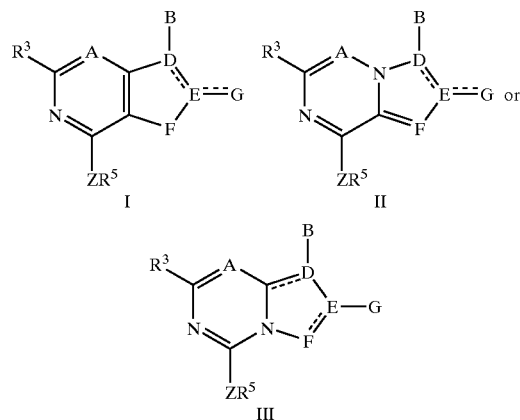

wherein the dashed lines, A, B, D E, F, Z, G, $R^3$, and $R^5$ having the definitions set forth in the specification pharmaceutical compositions containing them.

10 Claims, No Drawings

OTHER PUBLICATIONS

Fackelmann, K.A., and Raloff, J., Pycholgical Stress Linked to Cancer, Science News, (Sep. 25, 1993) vol. 144, p. 196.

Suda. et al., The role of corticotropin-releasing factor and vasopressin in hypoglycemia-induced pro-opiomelanocortin gene expression in the rat anterior pituitary gland, Brain Res. (1992), 579(2), pp. 303-308.

Sheharu, S. et al., Peripheral plasma corticortropin-releasing hormone (CHR) in an aged patient with fasting hypoglycemia associated with an insufficient secretion of insulin. An implication of plasma CRH in glucose metabolism, Nippon Naibunpi Gakkai Zasshi (1995), 71(5), pp. 659-672.

Reversibility of Physiological Growth Hormone Secretion in Children with Psychosocial Dwarfism, A. Albanese, et al., Clinical Endocrinology (1994) 40, pp. 687-692.

Psychosocial Dwarfism: Identification, Intervention and Planning, Bowden M. L.; Hopwood NJ Soc. Work Health Care (United States), Spring 1982, 7 (3) pp. 15-36.

Recent Advances in Antiviral Therapy, Kinchington D., J Clin Pathol, Feb. 1999, 52 (2) pp. 89-94.

The Role of Serotonin in Craving: From Basic Research to Human Studies, Ciccocioppo R., Alcohol & Alcoholism, vol. 34, No. 2, pp. 244-253, 1999.

EMBASE abstract No. 97225140 of Kapelle et al. (Kapelle et al., Pharmaceutisch Weekblad, (1997)).

* cited by examiner

SUBSTITUTED HETEROCYCLIC DERIVATIVES

This application claims the benefit of Provisional Application No. 60/008,396, filed Dec. 8, 1995.

BACKGROUND OF THE INVENTION

This invention relates to certain pharmaceutically active substituted heterocyclic derivatives, pharmaceutical compositions containing them and methods of administering them to subjects in need of their corticotropin releasing factor antagonist activity.

The substituted heterocyclic derivatives claimed in this case exhibit activity as corticotropin releasing factor CRF antagonists.

CRF antagonists are referred to in U.S. Pat. Nos. 4,605,642 and 5,063,245, which relate, respectively, to peptides and pyrazolinones, and were issued, respectively, on Aug. 12, 1986 and Nov. 5, 1991. They are also referred to in the following: PCT Patent Application PCT/IB95/00439, which designates the United States and was filed on Jun. 6, 1995; PCT Patent Application PCT/IB95/00373, which designates the United States and was filed on May 18, 1995; U.S. patent application Ser. No. 08/448,539, which was filed in the PCT on Nov. 12, 1993 and entered the U.S. national phase on Jun. 14, 1995; U.S. patent application Ser. No. 08/481,413, which was filed in the PCT on Nov. 26, 1993 and entered the U.S. national phase on Jul. 24, 1995; and U.S. patent application Ser. No. 08/254,820, which was filed on Apr. 19, 1995. All the foregoing patents and patent applications are incorporated herein by reference in their entireties.

The importance of CRF antagonists is discussed in the literature, e.g., as discussed in U.S. Pat. No. 5,063,245, which is incorporated herein by reference in its entirety. A recent outline of the different activities possessed by CRF antagonists is found in M. J. Owens et al., *Pharm. Rev., Vol.* 43, pages 425 to 473 (1991), also incorporated herein by reference. Based on the research described in these two and other references, CRF antagonists are effective in the treatment of a wide range of stress-related illnesses, such as depression, anxiety, headache, irritable bowel syndrome, inflammatory diseases, immune suppression, Alzheimer's disease, gastrointestinal diseases, anorexia nervosa, hemorrhagic stress, drug and alcohol withdrawal symptoms, drug addiction, infertility, head trauma, stroke, and stress-induced infections in humans and animals.

SUMMARY OF THE INVENTION

The present invention relates to compounds of the formula

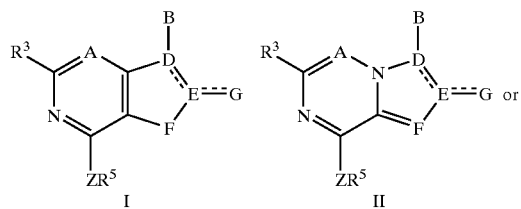

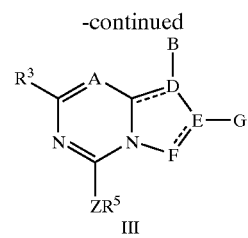

or a pharmaceutically acceptable salt thereof, wherein
the dashed lines represent optional double bonds;
A is nitrogen or $CR^7$;
B is $-NR^1R^2$, $-CR^1R^2R^{10}$, $-C(=CR^2R^{11})R^1$, $-NHCR^1R^2R^{10}$, $-OCR^1R^2R^{10}$, $-SCR^1R^2R^{10}$, $-CR^2R^{10}NHR^1$, $-CR^2R^{10}OR^1$, $-CR^2R^{10}SR^1$ or $-COR^2$;
D is nitrogen and is single bonded to all atoms to which it is attached, or D is carbon and is either double bonded to E in formulas I and II or double bonded to the adjacent carbon atom common to both fused rings in formula III, or D is CH and is single bonded to E in formulas I and II;
E is nitrogen, CH or carbon;
F is oxygen, sulfur, $CHR^4$ or $NR^4$ when it is single bonded to E and F is nitrogen or $CR^4$ when it is double bonded to E;
G, when single bonded to E, is hydrogen, $C_1-C_4$ alkyl, $-S(C_1-C_4$ alkyl), $-O(C_1-C_4$ alkyl), $NH_2$, $-NH(C_1-C_4$ alkyl) or $-N(C_1-C_2$ alkyl)$(C_1-C_4$ alkyl), wherein each of the $C_1-C_4$ alkyl groups of G may optionally be substituted with one hydroxy, $-O(C_1-C_2$ alkyl) or fluoro group; G, when double bonded to E, is oxygen, sulfur or NH; and G, when E is nitrogen and double bonded to D or F, is absent;
$R^1$ is hydrogen, $C_1-C_6$ alkyl optionally substituted with one or two substituents $R^8$ independently selected from hydroxy, fluoro, chloro, bromo, iodo, $C_1-C_4$ alkoxy, $CF_3$, $-C(=O)O-(C_1-C_4)$alkyl, $-OC(=O)(C_1-C_4$ alkyl), $-OC(=O)N(C_1-C_4$ alkyl)$(C_1-C_2$ alkyl), $-NHCO(C_1-C_4$ alkyl), $-COOH$, $-COO(C_1-C_4$ alkyl), $-CONH(C_1-C_4$ alkyl), $-CON(C_1-C_4$ alkyl)$(C_1-C_2$ alkyl), $-S(C_1-C_4$ alkyl), $-CN$, $-NO_2$, $-SO(C_1-C_4$ alkyl), $-SO_2(C_1-C_4$ alkyl), $-SO_2NH(C_1-C_4$ alkyl) and $-SO_2N(C_1-C_4$ alkyl)$(C_1-C_2$ alkyl), wherein each of the $C_1-C_4$ alkyl groups in the foregoing $R^1$ groups may optionally contain one or two double or triple bonds;
$R^2$ is $C_1-C_{12}$ alkyl which may optionally contain from one to three double or triple bonds, aryl or $(C_1-C_4$ alkylene) aryl, wherein said aryl and the aryl moiety of said $(C_1-C_4$ alkylene)aryl is selected from phenyl, naphthyl, thienyl, benzothienyl, pyridyl, quinolyl, pyrazinyl, pyrimidinyl, imidazolyl, furanyl, benzofuranyl, benzothiazolyl, isothiazolyl, pyrazolyl, pyrrolyl, indolyl, pyrrolopyridyl, oxazolyl and benzoxazolyl; $C_3-C_8$ cycloalkyl or $(C_1-C_6$ alkylene)$(C_3-C_8$ cycloalkyl), wherein one or two of the carbon atoms of said cycloalkyl and the 5 to 8 membered cycloalkyl moieties of said $(C_0-C_6$ alkylene)$(C_3-C_8$ cycloalkyl) may optionally and independently be replaced by an oxygen or sulfur atom or by $NZ^2$ wherein $Z^2$ is selected from hydrogen, $C_1-C_4$ alkyl, benzyl and $C_1-C_4$ alkanoyl, and wherein each of the foregoing $R^2$ groups may optionally be substituted with from one to three substituents independently selected from chloro, fluoro, hydroxy and $C_1$–$C_4$ alkyl, or with one substituent selected from bromo, iodo, $C_1$–$C_6$ alkoxy, —OC(=O)($C_1$–$C_6$ alkyl), —OC(=O)N($C_1$–$C_4$ alkyl)($C_1$–$C_2$ alkyl), —S($C_1$–$C_6$ alkyl), amino, —NH($C_1$–$C_2$ alkyl), —N($C_1$–$C_2$ alkyl)($C_1$–$C_4$ alkyl), —N($C_1$–$C_4$ alkyl)—CO—($C_1$–$C_4$ alkyl), —NHCO($C_1$–$C_4$ alkyl), —COOH, —COO($C_1$–$C_4$ alkyl), —CONH($C_1$–$C_4$ alkyl), —CON($C_1$–$C_4$ alkyl)($C_1$–$C_2$ alkyl), —SH, —CN, —NO$_2$, —SO($C_1$–$C_4$ alkyl), —SO$_2$($C_1$–$C_4$ alkyl), —SO$_2$NH($C_1$–$C_4$ alkyl) and —SO$_2$N($C_1$–$C_4$ alkyl)($C_1$–$C_2$ alkyl);

—NR$^1$R$^2$ or CR$^1$R$^2$R$^{10}$ may form a saturated 3 to 8 membered carbocyclic ring which may optionally contain from one to three double bonds and wherein one or two of the ring carbon atoms of such 5 to 8 membered rings may optionally and independently be replaced by an oxygen or sulfur atom or by NZ$^3$ wherein Z$^3$ is hydrogen, $C_1$–$C_4$ alkyl, benzyl or $C_1$–$C_4$ alkanoyl;

R$^3$ is hydrogen, $C_1$–$C_4$ alkyl, —O($C_1$–$C_4$ alkyl), chloro, fluoro, bromo, iodo, —CN, —S($C_1$–$C_4$ alkyl) or —SO$_2$($C_1$–$C_4$ alkyl) wherein each of the ($C_1$–$C_4$ alkyl) moieties in the foregoing R$^3$ groups may optionally be substituted with one substituent R$^9$ selected from hydroxy, fluoro and ($C_1$–$C_2$ alkoxy);

each R$^4$ is, independently, hydrogen, ($C_1$–$C_6$ alkyl), fluoro, chloro, bromo, iodo, trifluoromethyl, hydroxy, cyano, amino, nitro, —O($C_1$–$C_4$ alkyl), —N($C_1$–$C_4$ alkyl)($C_1$–$C_2$ alkyl), —S($C_1$–$C_4$ alkyl), —SO($C_1$–$C_4$ alkyl), —SO$_2$($C_1$–$C_4$)alkyl, —CO($C_1$–$C_4$ alkyl), —C(=O)H or —C(=O)O($C_1$–$C_4$alkyl), wherein each of the ($C_1$–$C_6$ alkyl) and ($C_1$–$C_4$ alkyl) moieties in the foregoing R$^4$ groups may optionally contain one or two double or triple bonds and may optionally be substituted with one or two substituents independently selected from hydroxy, amino, $C_1$–$C_3$ alkoxy, dimethylamino, methylamino, ethylamino, —NHC(=O)CH$_3$, fluoro, chloro, $C_1$–$C_3$ thioalkyl, —CN, —COOH, —C(=O)O($C_1$–$C_4$ alkyl), —C(=O)($C_1$–$C_4$ alkyl) and —NO$_2$;

R$^5$ is phenyl, naphthyl, thienyl, benzothienyl, pyridyl, pyrimidyl, quinolyl, pyrazinyl, furanyl, benzofuranyl, benzothiazolyl, benzisothiazolyl, benzisoxazolyl, benzimidazolyl, indolyl, benzoxazolyl or $C_3$–$C_8$ cycloalkyl wherein one or two of the carbon atoms of said cycloalkyl rings that contain at least 5 ring members may optionally and independently be replaced by an oxygen or sulfur atom or by NZ$^4$ wherein Z is hydrogen, $C_1$–$C_4$ alkyl or benzyl; and wherein each of the foregoing R$^5$ groups is substituted with from one to four substituents R$^{12}$ wherein one to three of said substituents may be selected, independently, from chloro, $C_1$–$C_6$ alkyl and —O($C_1$–$C_6$ alkyl) and one of said substituents may be selected from ($C_1$–$C_4$ alkyl) O($C_1$–$C_4$ alkyl), OCF$_3$, fluoro, bromo, iodo, formyl, —CN, —CF$_3$, —NO$_2$, —NH$_2$, —NH($C_1$–$C_4$ alkyl), —N($C_1$–$C_2$ alkyl)($C_1$–$C_6$ alkyl), —C(=O)O($C_1$–$C_4$ alkyl), —C(=O)($C_1$–$C_4$ alkyl), —COOH, —SO$_2$NH($C_1$–$C_4$ alkyl), —SO$_2$N($C_1$–$C_2$ alkyl)($C_1$–$C_4$ alkyl), —SO$_2$NH$_2$, —NHSO$_2$($C_1$–$C_4$ alkyl), —S($C_1$–$C_6$ alkyl) and —SO$_2$($C_1$–$C_6$ alkyl), and wherein each of the $C_1$–$C_4$ alkyl and $C_1$–$C_6$ alkyl moieties in the foregoing R$^5$ groups may optionally be substituted with one or two substituents independently selected from fluoro, hydroxy, amino, methylamino, dimethylamino and acetyl;

R$^7$ is hydrogen, $C_1$–$C_4$ alkyl, halo (e.g., chloro, fluoro, iodo or bromo), hydroxy, —O($C_1$–$C_4$ alykl), —C(=O)($C_1$–$C_4$ alkyl), —C(=O)O($C_1$–$C_4$ alkyl), —OCF$_3$, —CF$_3$, —CH$_2$OH or —CH$_2$O($C_1$–$C_2$ alkyl);

R$^{10}$ is hydrogen, hydroxy, methoxy or fluoro;

R$^{11}$ is hydrogen or $C_1$–$C_4$ alkyl; and

Z is NH, oxygen, sulfur, —N($C_1$–$C_4$ alkyl), —NC(=O)($C_1$–$C_2$ alkyl), NC(=O)O($C_1$–$C_2$alkyl) or CR$^{13}$R$^{14}$ wherein R$^{13}$ and R$^{14}$ are independently selected from hydrogen, trifluoromethyl and methyl with the exception that one of R$^{13}$ and R$^{14}$ can be cyano;

with the proviso that: (a) in the five membered rings of structures I, II and III, there can not be two double bonds adjacent to each other; and (b) when R$^4$ is attached to nitrogen, it is not halo, cyano or nitro.

Examples of more specific embodiments of formula I, II and III are the following, wherein A, B, G, Z, R$^3$, R$^4$ and R$^5$ are defined as above, X is NR$^4$, O, S or CR$^4$ and R$^{25}$ is hydrogen, ($C_1$–$C_4$)alkyl or CF$_3$.

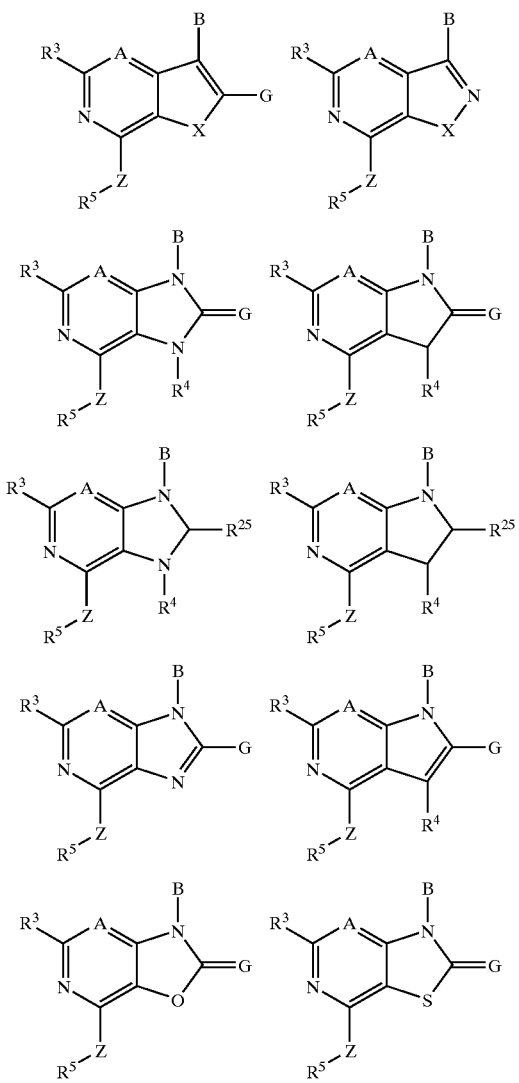

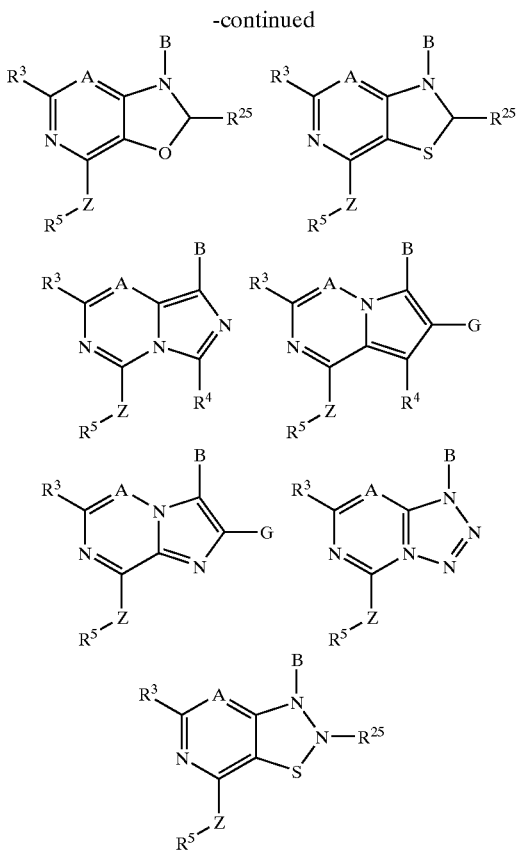

The compounds of formulas I, II and III may contain one or more chiral centers and may therefore occur in different isomeric forms. The invention includes all stereoisomers and diastereomers of such compounds of formulas I, II and III, including racemic and optically active mixtures thereof.

This invention also relates to the pharmaceutically acceptable acid and base addition salts of compounds of the formulas I, II and III. Examples of such pharmaceutically acceptable acid addition salts are the salts of hydrochloric acid, p-toluenesulfonic acid, maleic acid, fumaric acid, citric acid, succinic acid, salicylic acid, oxalic acid, hydrobromic acid, phosphoric acid, methanesulfonic acid, tartaric acid, di-p-toluoyl tartaric acid, and mandelic acid. Examples of such pharmaceutically acceptable base addition salts are the salts of the alkali metals and alkaline earth metals.

More specific embodiments of this invention include compounds of the above formulas I, II and III wherein: $R^1$ is $C_1$–$C_6$ alkyl, which may optionally be substituted with one hydroxy, fluoro, $CF_3$, or $C_1$–$C_4$ alkoxy group and may optionally contain one double or triple bond; and $R^2$ is benzyl, $C_1$–$C_6$ alkyl, which may optionally contain one double or triple bond, wherein said $C_1$–$C_6$ alkyl and the phenyl moiety of said benzyl may optionally be substituted with one fluoro, $CF_3$, $C_1$–$C_2$ alkyl, $C_1$–$C_2$ alkoxy or chloro group.

Other more specific embodiments of the invention include compounds of formulas I, II and III wherein $R^3$ is methyl, ethyl, chloro or methoxy; $R^4$ is methyl, ethyl or trifluoromethyl; G is hydrogen, methyl, ethyl, or E=G is C=O, C=S; $R^5$ is phenyl, pyridyl, pyrimidyl which is substituted with more than two substituents independently selected from $C_1$–$C_4$ alkyl, —O($C_1$–$C_4$ alkyl), ($C_1$–$C_4$ alkyl)—O—($C_1$–$C_4$ alkyl), $CF_3$, $OCF_3$, —CHO, ($C_1$–$C_4$ alkyl)—OH, CN, Cl, F, Br, I and $NO_2$, wherein each of the foregoing ($C_1$–$C_4$) alkyl groups may optionally contain one double or triple bond.

Other more specific embodiments of the invention include compounds of the formulas I, II and III wherein A is N, CH or CMe.

Examples of preferred compounds of this invention are:
2,5,6-trimethyl-7-(1-propylbutyl)-4-(2,4,6-trimethylphenoxy)-7H-pyrrolo[2,3-d]pyrimidine;
1-(1-ethylpropyl)-6-methyl-4-(2,4,6-trimethylphenylamino)-1,3-dihydro-imidazo[4,5-c]pyridin-2-one;
9-(1-ethylpropyl)-2-methyl-6-(2,4,6-trimethylphenylamino)-7,9-dihydro-purin-8-one;
1-(1-ethylpropyl)-6-methyl-4-(2,4,6-trimethylphenoxy)-1,3-dihydro-imidazo[4,5-c]pyridin-2-one;
1-(1 ethylpropyl)-6-methyl-4-(2,4,6-trimethylphenoxy)-1H-imidazo[4,5-c]pyridine;
1-(1-ethylpropyl)-3,6-dimethyl-4-(2,4,6-trimethylphenoxy)-1,3-dihydro-imidazo[4,5-c]pyridin-2-one; and
1-(1-ethylpropyl)-3,6-dimethyl-4-(2,4,6-trimethylphenylamino)-1,3-dihydro-imidazo[4,5-c]pyridin-2-one.

Examples of other compounds of this invention are:
[2,6-dimethyl-4-(2,4,6-trimethylphenoxy)-thien[3,2-d]pyrimidin-7-yl]diethylamine;
[2,6-dimethyl-4-(2,4,6-trimethylphenoxy)-thien[3,2-d]pyrimidin-7-yl]ethylpropyl-amine;
[2,6-dimethyl-4-(2,6-dimethyl-4-chlorophenoxy)-thien[3,2-d]pyrimidin-7-yl]diethyl-amine;
[2,6-dimethyl-4-(2,6-dimethyl-4-chlorophenoxy)-thien[3,2-d]pyrimidin-7-yl]ethyl-propylamine;
[2,6-dimethyl-4-(2,6-dimethyl-bromo-phenoxy)-thien[3,2-d]pyrimidin-7-yl]diethyl-amine;
[2,6-dimethyl-4-(2,6-dimethyl-4-bromophenoxy)-thien[3,2-d]pyrimidin-7-yl]ethyl-propylamine;
[2-methyl-4-(2,4,6-trimethylphenoxy)-thien[3,2-d]pyrimidin-7-yl]diethyl-amine;
3-(1-ethylpropyl)-2,5-dimethyl-7-(2,4,6-trimethylphenoxy)-thien[2,3-c]pyridine;
[3-(1-ethylpropyl)-2,5-dimethyl-thien[2,3-c]pyridin-7-yl]-(2,4,6-trimethylphenyl)-amine;
3-(1-ethylpropyl)-2,5-dimethyl-7-(2,4,6-trimethylphenoxy)-furo[2,3-c]pyridine;
[3-(1-ethylpropyl)-2,5-dimethyl-furo[2,3-c]pyridin-7-yl]-(2,4,6-trimethylphenyl)-amine;
[1-(1-ethylpropyl)-2,6-dimethyl-4-(2,4,6-trimethylphenoxy)-1H-pyrrolo[3,2-c]pyridine;
[1-(1-ethylpropyl)-2,6-dimethyl-1H-pyrrolo[3,2-c]pyridin-4-yl]-(2,4,6-trimethylphenyl)amine;
[1-(1-ethylpropyl)-3,6-dimethyl-1H-pyrrolo[3,2-c]pyridin-4-yl]-(2,4,6-trimethylphenyl)amine;
[1-(1-ethylpropyl)-6-methyl-1H-pyrrolo[3,2-c]pyridin-4-yl]-(2,4,6-trimethylphenyl)-amine;
[1-(1-ethylpropyl)-6-methyl-4-(2,4,6-trimethylphenoxy)-1H-pyrazolo[4,3-c]pyridine;
[1-(1-ethylpropyl)-3,6-dimethyl-4-(2,4,6-trimethylphenoxy)-1H-pyrazolo[4,3-c]pyridine;
[1-(1-ethylpropyl)-3,6-dimethyl-1H-pyrazolo[4,3-c]pyridin-4-yl]-(2,4,6-trimethyl-phenyl)amine;
[1-(1-ethylpropyl)-6-methyl-1 H-pyrazolo[4,3-c]pyridinyl]-(2,4,6-trimethylphenyl)-amine;
[3-(1-ethylpropyl)+methylisoxazolo[4,5-d]pyrimidin-7-yl]-(2,4,6-trimethylphenyl)-amine;
[3-(1-ethylpropyl)-5-methylisoxazolo[5,4-c]pyridin-7-yl]-(2,4,6-trimethylphenyl)-amine;
[3-(1-ethylpropyl)-5-methylisothiazolo[4,5-d]pyrimidin-7-yl]-(2,4,6-trimethylphenyl)amine;

[3-(1-ethylpropyl)-5-methylisothiazolo[5,4-c]pyridin-7-yl]-(2,4,6-trimethylphenyl)-amine;
diethyl-[5-methyl-7-(2,4,6-trimethylphenoxy)-isothiazolo[5,4-c]pyridin-3-yl]amine;
N3,N3-diethyl-[5-methyl-N-7-(2,4,6-trimethylphenyl)-isothiazolo[5,4-c]pyridin-3,7-diamine;
N3,N3-diethyl-[5-methyl-N-7-(2,4,6-trimethylphenyl)-isoxzolo[5,4-c]pyridin-3,7-diamine;
1-(1-ethylpropyl)-6-methyl-4-(2,4,6-trimethylphenoxy)-1H-[1,2,3]triazolo[4,5-c]pyridine;
1-(1-ethylpropyl)-6-methyl-4-(2,4,6-trimethylphenylsulfanyl)-1H-[1,2,3]triazolo[4,5-c-]pyridine;
3-(1-ethylpropyl)-1,5-dimethyl-7-(2,4,6-trimethylbenzyl)-1H-pyrrolo[2,3-c]pyridine;
3-(1-ethylpropyl)-1,5-dimethyl-7-(2,4,6-trimethylbenzyl)-1H-pyrrolo[3,2-d]pyrimidine;
5-(1-ethylpropyl)-3,6-dimethyl-1-(2,4,6-trimethylphenoxy)-pyrrolo[1,2-c]pyridine;
N6,N6-diethyl-3,7-dimethyl-N-1-(2,4,6-trimethylphenyl)-pyrrolo[1,2-a]pyrazine-1,6-diamine;
6-(1-ethylpropyl)-3,7-dimethyl-1-(2,4,6-trimethylphenoxy)-pyrrolo[1,2-a]pyrazine;
1-(1-ethylpropyl)-6-methyl-4-(2,4,6-trimethylphenoxy)-1H-[1,2,3]triazolo[4,5-c]pyridine;
diethyl-[3,7-dimethyl-N  1-(2,4,6-trimethylphenoxy)-pyrrolo[1,2-a]pyrazin-6-yl]-amine;
[1-(ethylpropyl)-3,7-dimethyl-imidazo[1,5-c]pyrimidin-5-yl]-(2,4,6-trimethylphenyl)amine;
7-Bromo-1-(1  ethyl-propyl)-6-methyl-4-(2,4,6-trimethylphenoxy)-1H-[1,2,3]triazolo[4,5-c]pyridine;
1-(1-Ethyl-propyl)-6,7-dimethyl-4-(2,4,6-trimethyl-phenoxy)-1H-[1,2,3]triazolo[4,5-c]pyridine;
1-(1-Ethyl-propyl)-6-methyl-4-(2,4,6-trimethyl-phenoxy)-1,3-dihydro-pyrrolo-[3,2-c]pyridin-2-one;
1-(1-Ethyl-propyl)-6-methyl-4-(2,4,6-trimethyl-phenoxy)-1H-pyrrolo[3,2-c]pyridine;
1-(1-Ethyl-propyl)-6-methyl-4-(2,4,6-trimethyl-phenoxy)-2,3-dihydro-1H-pyrrolo [3,2-c]pyridine;
1-(1-Ethyl-propyl)-6-methyl-4-(2,4,6-trimethyl-phenoxy)-1H-imidazo[4,5-c]pyridin-2-ylamine;
1-(1-Ethyl-propyl)-3,6-dimethyl-4-(2,4,6-trimethyl-phenoxy)-1,3-dihydro-pyrrolo [3,2-c]pyridin-2-one;
1-(1-Ethyl-propyl)-3,3,6-trimethyl-4-(2,4,6-trimethyl-phenoxy)-1,3-dihydro-pyrrolo[3,2-c]pyridin-2-one;
1-(1-Ethyl-propyl)-3,3,6-trimethyl-4-(2,4,6-trimethyl-phenoxy)-2,3-dihydro-1H-pyrrolo[3,2-c]pyridine;
1-(1-Ethyl-propyl)-3,6-dimethyl-4-(2,4,6-trimethyl-phenoxy)-1 H-pyrrolo[3,2-c]pyridine;
1-(1-Ethyl-propyl)-2-methoxy-3,6-dimethyl-4-(2,4,6-trimethyl-phenoxy)-1H-pyrrolo[3,2-c]pyridine;
[1-(1-Ethyl-propyl)-6-methyl-1H-[1,2,3]triazolo[4,5-c]pyridin-4-yl]-(2,4,6-trimethyl-phenyl)-amine;
4-(4-Bromo-2,6-dimethyl-phenoxy)-1-(1-ethyl-propyl)-6-methyl-1 H-oxazolo[5,4-c]pyridin-2-one;
1-(1-Ethyl-propyl)-6-methyl-4-(2,4,6-trimethyl-phenoxy)-1 H-oxazolo[5,4-c]pyridin-2-one;
1-(1-Ethyl-propyl)-3,6-dimethyl-4-(4-chloro-2,6-dimethyl-phenoxy)-1H-pyrrolo[3,2-c]pyridine;
1-(1-Ethyl-propyl)-3,6-dimethyl-4-(4-bromo-2,6-dimethyl-phenoxy)-1H-pyrrolo[3,2-c]pyridine;
1-(1-Ethyl-propyl)-3,6-dimethyl-4-(4-i-propyl-2,6-dimethyl-phenoxy)-1H-pyrrolo[3,2-c]pyridine;
1-(1-Ethyl-propyl)-3,6-dimethyl-4-(4-t-butyl-2,6-dimethyl-phenoxy)-1H-pyrrolo[3,2-c]pyridine;
1-(1-Ethyl-propyl)-3,6-dimethyl-4-(4-ethyl-2,6-dimethyl-phenoxy)-1H-pyrrolo[3,2-c]pyridine;
1-(1-Ethyl-propyl)-3,6-dimethyl-4-(4-propyl-2,6-dimethyl-phenoxy)-1H-pyrrolo[3,2-c]pyridine;
1-(1-Ethyl-propyl)-3,6-dimethyl-4-(4-trifluoro-2,6-dimethyl-phenoxy)-1H-pyrrolo[3,2-c]pyridine;
1-(1-Ethyl-propyl)-3,6-dimethyl-4-(4-methoxymethyl-2,6-dimethyl-phenoxy)-1H-pyrrolo[3,2-c]pyridine;
1-(1-Ethyl-propyl)-3,6-dimethyl-4-(4-hydroxymethyl-2,6-dimethyl-phenoxy)-1H-pyrrolo[3,2-c]pyridine;
1-(1-Ethyl-propyl)-3,6-dimethyl-4-(4-formyl-2,6-dimethyl-phenoxy)-1H-pyrrolo[3,2-c]pyridine;
1-(1-Ethyl-propyl)-3,6-dimethyl-4-(2-bromo-4-i-propyl-phenoxy)-1H-pyrrolo[3,2-c]pyridine;
1-(1-Ethyl-propyl)-3,6-dimethyl-4-(2,4-dimethyl-phenoxy)-1H-pyrrolo[3,2-c]pyridine;
1-(1-Ethyl-propyl)-3-ethyl-6-methyl-4-(2,6-dimethyl-4-chloro-phenoxy)-1H-pyrrolo[3,2-c]pyridine;
2-[4-(4-Chloro-2,6-dimethyl-phenoxy)-3,6-dimethyl-pyrrolo[3,2-c]pyridin-1-yl]-butan-1-ol;
2-[4-(4-bromo-2,6-dimethyl-phenoxy)-3,6-dimethyl-pyrrolo[3,2-c]pyridin-1-yl]butan-1-ol;
2-[4-(4-i-propyl-2,6-dimethyl-phenoxy)-3,6-dimethyl-pyrrolo[3,2-c]pyridin-1-yl]butan-1-ol;
2-[4-(4-Ethyl-2,6-dimethyl-phenoxy)-3,6-dimethyl-pyrrolo[3,2-c]pyridin-1-yl]butan-1-ol;
2-[4-(4-trifluoromehtyl-2,6-dimethyl-phenoxy)-3,6-dimethyl-pyrrolo[3,2-c]pyridin-1-yl]-butan-1-ol;
2-[4-(2-bromo-4-i-propyl-phenoxy)-3,6-dimethyl-pyrrolo[3,2-c]pyridin-1-yl]butan-1-ol.

Whenever reference is made herein to $C_1$–$C_6$ alkyl, a straight or branched chain alkyl of one to six carbon atoms is meant, such as methyl, ethyl, isopropyl, t-butyl or hexyl.

Whenever $R^2$ or $R^5$ is a heterocyclic group, attachment of the group is through a carbon atom.

Whenever reference is made herein to $C_1$–$C_4$ alkyl or $C_1$–$C_6$ alkyl which "may contain one double or triple bond" in the definitions of $R^1$ and $R^4$, it is understood that at least two carbons are present in the alkyl for one double or triple bond.

Whenever reference is made herein to halo or halogen, fluoro, chloro, bromo or iodo is meant unless indicated otherwise.

This invention also relates to a pharmaceutical composition for the treatment or prevention of (a) a disorder, the treatment of which can be effected or facilitated by antagonizing CRF, including but not limited to disorders induced or facilitated by CRF, or (b) a disorder selected from inflammatory disorders such as rheumatoid arthritis and osteoarthritis, pain, asthma, psoriasis and allergies; generalized anxiety disorder; panic; phobias; obsessive-compulsive disorder; post-traumatic stress disorder; sleep disorders induced by stress; pain perception such as fibromyalgia; mood disorders such as depression, including major depression, single episode depression, recurrent depression, child abuse induced depression, and postpartum depression; dysthemia; bipolar disorders; cyclothymia; fatigue syndrome; stress-induced headache; cancer; human immunodeficiency virus (HIV) infections; neurodegenerative diseases such as Alzheimer's disease, Parkinson's disease and Huntington's disease; gastrointestinal disorders such as ulcers, irritable bowel syndrome, Crohn's disease, spastic colon, diarrhea, and post operative ilius and colonic hypersensitivity associated with psychopathological disturbances or stress; eating disorders such as anorexia and bulimia nervosa; hemorrhagic stress; chemical dependencies and addictions (e.g., dependencies on alcohol, cocaine, heroin, benzodiazepines, or other drugs); drug and alcohol withdrawal symptoms; stress-induced psychotic episodes; euthyroid sick syndrome; syndrome of inappropriate antidiarrhetic hormone (ADH); obesity; infertility; head traumas; spinal cord trauma; ischemic neuronal damage (e.g., cerebral ischemia such as cerebral hippocampal ischemia); excitotoxic neuronal damage; epilepsy; cardiovascular and heart related disorders including hypertension, tachycardia and congestive heart failure; stroke; immune dysfunctions including stress induced immune dysfunctions (e.g., stress induced fevers, porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; osteoporosis; psychosocial dwarfism; and hypoglycemia in a mammal, including a human, comprising an amount of a compound of the formula I, II or III, or a pharmaceutically acceptable salt thereof, that is effective in the treatment or prevention of such disorder, and a pharmaceutically acceptable carrier.

This invention also relates to a pharmaceutical composition for the prevention or premature births in a mammal, including a human, comprising an amount of a compound of the formula I, II or III, or a pharmaceutically acceptable salt thereof, that is effective in the prevention of such disorder, and a pharmaceutically acceptable carrier.

This invention further includes a method for the treatment or prevention of (a) a disorder, the treatment of which can be effected or facilitated by antagonizing CRF, including but not limited to disorders induced or facilitator by CRF, or (b) a disorder selected from inflammatory disorders such as rheumatoid arthritis and osteoarthritis, pain, asthma, psoriasis and allergies; generalized anxiety disorder; panic; phobias; obsessive-compulsive disorder; post-traumatic stress disorder; sleep disorders induced by stress; pain perception such as fibromyalgia; mood disorders such as depression, including major depression, single episode depression, recurrent depression, child abuse induced depression, and postpartum depression; dysthemia; bipolar disorders; cyclothymia; fatigue syndrome; stress-induced headache; cancer; human immunodeficiency virus (HIV) infections; neurodegenerative diseases such as Alzheimer's disease, Parkinson's disease and Huntington's disease; gastrointestinal diseases such as ulcers, irritable bowel syndrome, Crohn's disease, spastic colon, diarrhea, and post operative ilius and colonic hypersensitivity associated with psychopathological disturbances or stress; eating disorders such as anorexia and bulimia nervosa; hemorrhagic stress; stress-induced psychotic episodes; euthyroid sick syndrome; syndrome of inappropriate antidiarrhetic hormone (ADH); obesity; infertility; head traumas; spinal cord trauma; ischemic neuronal damage (e.g., cerebral ischemia such as cerebral hippocampal ischemia); excitotoxic neuronal damage; epilepsy; cardiovascular and heart related disorders including hypertension, tachycardia and congestive heart failure; stroke; immune dysfunctions including stress induced immune dysfunctions (e.g., stress induced fevers, porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; chemical dependencies and addictions (e.g., dependencies on alcohol, cocaine, heroin, benzodiazepines, or other drugs); drug and alcohol withdrawal symptoms; osteoporosis; psychosocial dwarfism and hypoglycemia in a mammal, including a human, comprising administering to a subject in need of said treatment an amount of a compound of the formula I, II or III, or a pharmaceutically acceptable salt thereof, that is effective in treating or preventing such disorder.

This invention also relates to a method of preventing premature births in a mammal, including a human, comprising administering to said mammal an amount of a compound of the formula I, II or III, or a pharmaceutically acceptable salt thereof, that is effective in preventing such disorder.

DETAILED DESCRIPTION OF THE INVENTION

The following compounds having the formulas IV, V and VI are useful as starting materials and intermediates in the synthesis of compounds of the formulas I, II and III.

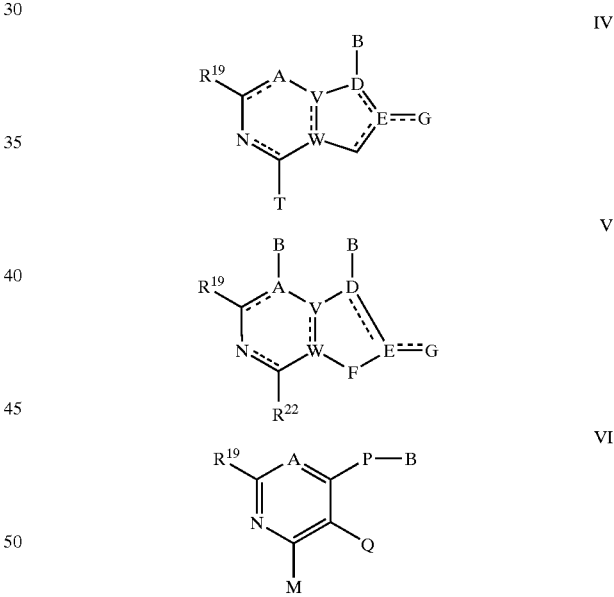

In the above compounds of formulas IV, V and VI, $R^{19}$ is $(C_1-C_4)$alkyl, fluoro, chloro, bromo or iodo, T is chloro, bromo, iodo, —OCOCF$_3$ or —OSO$_2$CF$_3$, M is T or $ZR^5$, $R^{22}$ is OH or NH$_2$, P is NH, CHCN or CHCOO($C_1$–$C_4$ alkyl), Q is —NH$_2$, —CH$_2$COO($C_1$–$C_4$alkyl), CH$_2$CN, —OH or —SH, V and W are, independently, C or N, but cannot both be N, and A, B, D, E, F and G are defined as above.

Methods of preparing the compounds and compositions of this invention are described below. In the discussion and reaction schemes that follow, $R^1$ through $R^5$, $R^7$ through $R^{14}$, $R^{19}$, $R^{25}$ A, B, D, E, F, G, X, the dashed lines and structural formulas I, II, III, IV, V and VI, unless otherwise indicated, are defined as above.

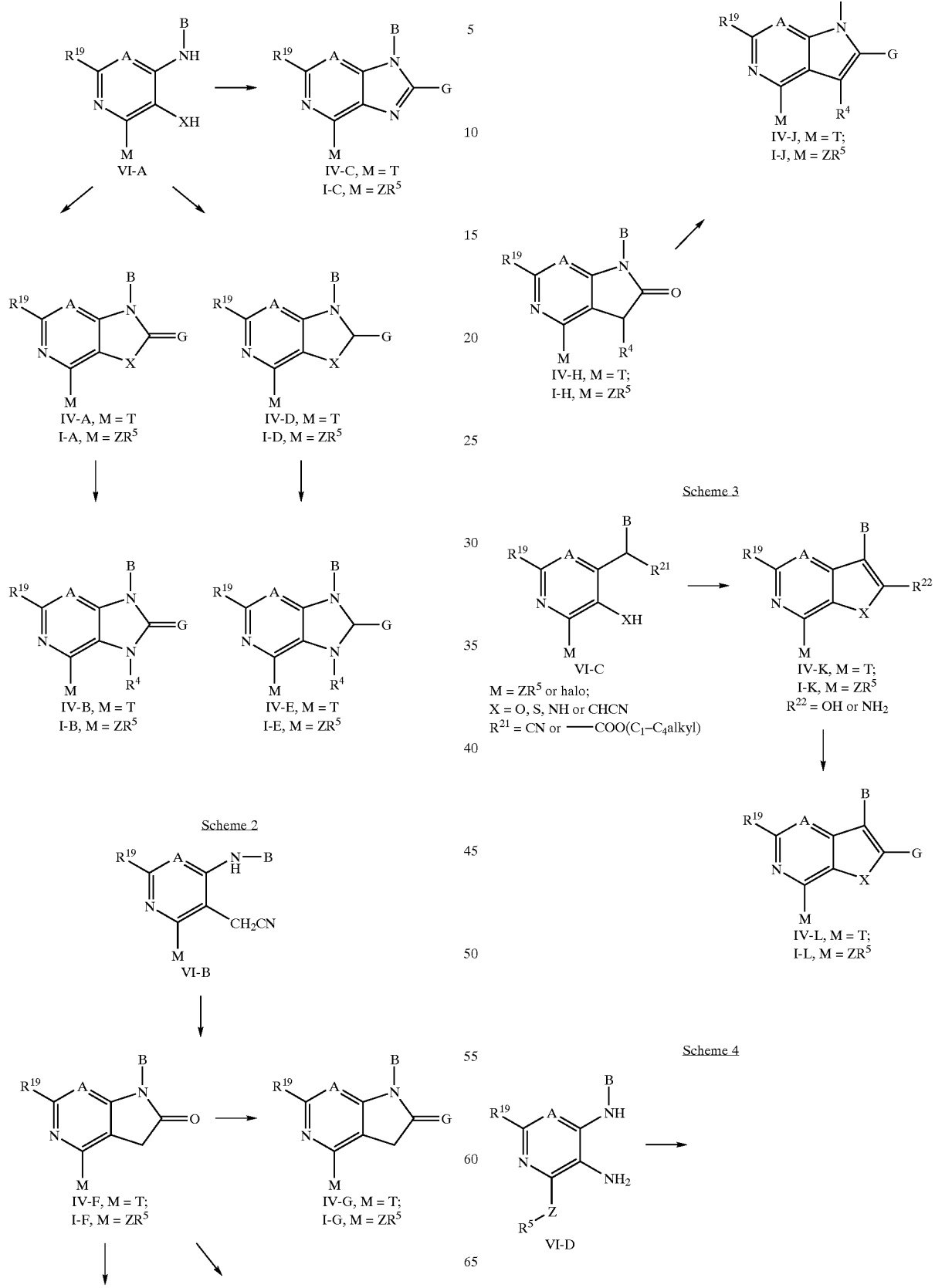

-continued

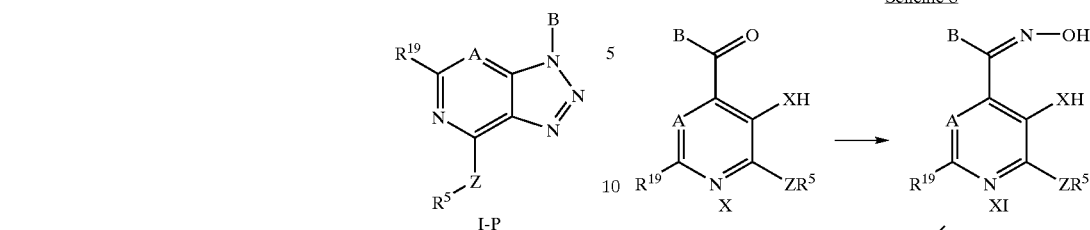
I-P

Scheme 5

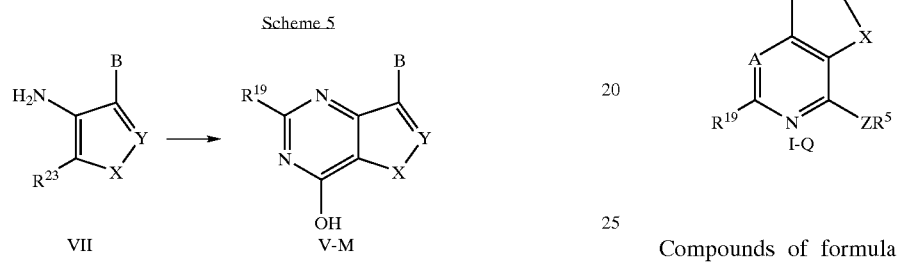
VII → V-M

X = NH or N(C$_1$–C$_4$ alkyl);
Y = N, CH or C(C$_1$–C$_4$ alkyl);
R$^{23}$ = —CN, —CONH$_2$, or —COO(C$_1$–C$_4$ alkyl)

Scheme 6

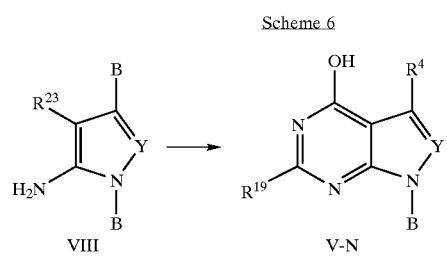
VIII → V-N

R$^{23}$ = —CN, —CONH$_2$, or —COO(C$_1$–C$_4$ alkyl);
Y = N or C-G

Scheme 7

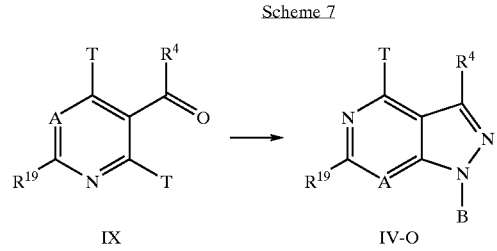
IX → IV-O

Scheme 8

[Scheme 8 structures: X → XI → I-Q]

Compounds of formulas I, II, and III wherein R$^3$ is C$_1$–C$_4$alkyl, fluoro, chloro, bromo, or iodo (hereinafter R$^{19}$) may be prepared by reaction of a compound of formula IV, wherein T is Cl, Br, I, —O—COCF$_3$, —OSO$_2$CF$_3$, V and W are, independently, C or N and V and W are not both N, and A, T, D, E, F, and G are defined as above with reference of formulas I, II, and III, with a compound of formula R$^5$ZH wherein Z and R$^5$ are as defined above. This reaction is generally carried out with or without a solvent, in the presence of a base, at a temperature from about 0° C. to about 270° C., and at a pressure between about 1 atmosphere and 300 psi. Suitable solvents include organic solvents such as tetrahydrofuran (THF), acetonitrile, dimethylsulfoxide (DMSO), acetone, C$_2$–C$_{15}$ alcohols, chloroform, dioxane, chlorobenzene, benzene, toluene, xylene, sulfolane, pyridine, quinoline, 2,4,6-trimethylpyridine, acetamide, di-(C$_1$–C$_2$)alkylacetamide, or 1-methyl-2-pyrrolidinone (NMP).

When Z is NH, an excess of R$^5$ZH may be used both as a reagent and as a base. Examples of bases other than R$^5$ZH that may be used include potassium carbonate, sodium hydride, potassium hydride, sodium (C$_1$–C$_4$) alkoxides, potassium (C$_1$–C$_4$) alkoxides, sodium, sodium amide, tri-[(C$_1$–C$_6$) alkyl]amines, organolithium or organosodium compounds such as n-butyllithium, s-butyllithium, t-butyllithium, lithium diisopropylamide, lithium bis(trimethylsilyl)amide, sodium diisopropylamide or sodium bis(trimethylsilyl)amide, and organometallic bases such as Grignard reagents. This reaction is generally carried out in an appropriate solvent (e.g., THF, dioxane, sulfolane, DMSO or NMP, with or without an additional catalyst such as a copper halide, oxide or sulfate (e.g., CuI, CuBr, Cu$_2$O, CuCl, CuSO$_4$, CuI$_2$, CuBr$_2$, CuCl$_2$ or Cu(O)), a Pd(O) salt such as tetrakis(triphenylphosphine)palladium (Pd(PPH$_3$)$_4$), a Pd(II) salt such as palladium diacetate (Pd(OAc)$_2$) or racemic or (R)- or (S)-2,2'-bis(diphenylphosphino)-1,1'-binaphthyl (BINAP), at temperature from about room temperature to about 270° C.

When Z is O or S, a base which is capable of deprotonating $R^5ZH$ may be used, such as potassium carbonate, sodium carbonate, sodium amide, an alkali metal hydride such as sodium or potassium hydride, a sodium $C_1-C_4$ alkoxide, a potassium $C_1-C_4$ alkoxide, sodium amide, a tri-($C_1-C_6$alkyl)amine or an organometallic base such as n-butyllithium, s-butyllithium, t-butyllithium, lithium diisopropylamide, lithium bis(trimethylsilyl)amide, sodium diisopropylamide or sodium bis(trimethylsilyl)amide. The reaction temperature can range from about 0° C. to about 180° C. and is preferably from about 50° C. to about 140° C. Suitable solvents include DMSO, THF, sulfolane, dioxane and NMP.

When Z is CHCN or CHCOO($C_1-C_4$ alkyl), a base that is capable of deprotonating $R^5ZH$ may be used, such as an alkali metal hydride (e.g., sodium or potassium hydride), a sodium $C_1-C_4$ alkoxide or an organometallic base such as n-butyllithium, s-butyllithium, t-butyllithium, lithium diisopropylamide, lithium bis(trimethylsilyl)amide, sodium diisopropylamide or sodium bis(trimethylsilyl)amide, in an appropriate solvent, e.g., a solvent selected from THF, DMSO, dioxane, methylene chloride ($CH_2Cl_2$), chloroform ($CHCl_3$), toluene, xylene, benzene and $C_1-C_6$ alkanols.

Compounds of the formulas I, II and III wherein Z is $CR^{13}CN$, $CHR^{13}$, $N(C_1-C_4$ alkyl), $NC(=O)(C_1-C_2$ alkyl) and $NC(=O)O(C_1-C_2$ alkyl) may be prepared as described below, using methods that are well known in the art.

When Z is $CR^{13}CN$, compounds of formulas I, II, and III may be prepared by reaction of the corresponding compounds wherein Z is CHCN with a base such as an alkali metal hydride such as sodium or potassium hydride, n-butyllithium, s-butyllithium, t-butyllithium, lithium diisopropylamide, lithium bis(trimethylsilyl)amide or sodium diisopropylamide, followed by reacting with a compound of the formula $R^{13}L$ wherein L is a leaving group such as I, Br, Cl, mesylate (OMs) or tosylate (OTs).

Compounds of the formulas I, II and III wherein Z is $CHR^{13}$ may be prepared by acid hydrolysis (using, e.g., 85% phosphoric acid) of the corresponding compounds wherein Z is $CR^{13}CN$, followed by decarboxylation upon heating. Further alkylation in the presence of base and a compound of the formula and $R^{14}L$, wherein L is defined as above, will yield the corresponding compounds of formulas I, II and III wherein Z is $CR^{13}R^{14}$.

When Z is $N(C_1-C_4$ alkyl), compounds of the formulas I, II and III may be prepared by reaction of the corresponding compounds wherein Z is NH with a base, followed by reaction with a compound of the formula ($C_1-C_4$ alkyl)-L, wherein L is defined as above. Bases such as lithium diisopropylamide, lithium bis(trimethylsilyl)amide, sodium diisopropylamide may also be used.

When Z is $NC(=O)(C_1-C_2$ alkyl) or $NC(=O)O(C_1-C_2$ alkyl), compounds of the formulas I, II, and III may be prepared by reaction of the corresponding compounds wherein Z is NH with a compound of the formula [($C_1-C_2$ alkyl)-C(=O)]$_2$O, ($C_1-C_2$ alkyl)-C(=O)(Cl) or ($C_1-C_2$ alkyl)—O—C(=O)(Cl) in the presence of base such as a tri($C_1-C_6$ alkyl)amine or pyridine.

Compounds of formulas I, II, and III, wherein Z and $R^5$ are defined with reference formulas I, II, and III above and $R^3$ is —O—($C_1-C_4$ alkyl) or —S—($C_1-C_4$ alkyl) (hereinafter $R^{20}$), may be prepared by reacting the corresponding compounds of the formulas I, II, and III, wherein $R^3$ is chloro, bromo, OTs or iodo, with a nucleophile of the formula $R^{20}H$, wherein $R^{20}H$ is an alkanol or an alkane thiol, optionally in the presence of an organic or inorganic base. Suitable bases include sodium, sodium hydride, potassium hydride, lithium diisopropylamide, lithium bis(trimethylsilyl)amide and sodium diisopropylamide.

Compounds of the formulas I, II, or III wherein $R^3$ is fluoro may be prepared by reacting the corresponding compounds wherein $R^3$ is chloro, bromo, iodo, —OCOCF$_3$, or —OSO$_2$CF$_3$ with tetrabutylammonium fluoride, potassium fluoride or another fluoride agent, using procedures well known to those skilled in the art. Compounds of the formulas I, II, or III wherein $R^3$ is CN may be prepared by reacting the corresponding compounds of formulas I, II, or III wherein $R^3$ is chloro, bromo, iodo, —OCOCF$_3$, or —OSO$_2$CF$_3$ with sodium cyanide, potassium cyanide, copper cyanide or other cyanide agent, using methods well known to those of skill in the art.

When $R^{22}$ is OH, compounds of formula IV may be prepared from compounds of formula V. When T is Cl, the compound of formula IV may be prepared by heating a compound of formula V with an excess of POCl$_3$, POCl$_3$/PCl$_5$ or PCl$_5$ at a temperature from about 80° C. to about 150° C., preferably at about the reflux temperature. When T is Cl, Br, or I, the compound of formula IV may be prepared by reacting the corresponding compound of formula IV wherein T is —OCOCF$_3$ or —OSO$_2$CF$_3$, preferably —OSO$_2$CF$_3$, with a sodium, potassium, or lithium halide in a suitable solvent such as sulfolane, DMSO or 1-methyl-2-pyrrolidinone. Compounds of formula IV wherein T is —OCOCF$_3$ or —OSO$_2$CF$_3$ may be prepared by reacting a compound of formula V with (CF$_3$CO)$_2$O, (CF$_3$SO$_2$)$_2$O, CF$_3$SO$_2$Cl, or CF$_3$COCl, with or without a base. Suitable bases include tri-($C_1-C_6$ alkyl)amines and sodium and potassium carbonates. When $R^3$ is chloro, bromo, iodo, —OCOCF$_3$, or —OSO$_2$CF$_3$, it is preferable for $R^3$ and T to be the same.

When $R^{22}$ is NH$_2$, compounds of the formula IV may be prepared by reacting a compound of the formula V with a compound of the formula ($C_1-C_4$ alkyl)—O—N=O and a copper (II) halide in an appropriate solvent such as acetonitrile, acetone, toluene, methylene chloride or dichloroethane, at a temperature from about room temperature to about the reflux temperature. This reaction is preferably carried out in acetonitrile at the reflux temperature.

Alternatively, as shown in Scheme I, compounds of the formulas I-A, I-C and I-D may be prepared from compounds of the formula VI-A. Referring to Scheme 1, reaction of a compound of the formula VI-A (wherein M is T or ZR$^5$, T is Cl, Br, I, OTs or —OCOCF$_3$, X is O, NH, NR$^4$, or S, and A, B, and $R^{19}$ are defined as above) with phosgene or its equivalent (e.g., diphosgene or triphosgene), thiophosgene, or CNBr, in the presence of a base such as a tri-($C_1-C_4$) alkylamine or sodium hydride, in an appropriate solvent (e.g., methylene chloride, chloroform or THF) in the presence of a tri($C_1-C_4$ alkyl)amine, will yield compounds of the formula IV-A wherein M is T and G is O, S, or NH, or the corresponding compounds of the formula I-A wherein M is ZR$^5$. Compounds of formula I-C and IV-C may be prepared by heating compounds of formula VI-A with a compound of the formula ($C_1-C_4$ alkyl)-C-[O($C_1-C_2$ alkyl)]$_3$ or HC[O—($C_1-C_2$)alkyl]$_3$ in the presence of a catalytic amount of acid (e.g., p-toluene sulfonic, conc. sulfuric acid or gaseous hydrogen chloride), in an appropriate solvent such as toluene, benzene or xylene, under a Dean-Stark trap. Compounds of the formula I-D wherein G is hydrogen or $C_1-C_4$ alkyl may be prepared by heating a compound of the formula GCHO or GH(OMe)$_2$ in the presence of an acid catalyst.

Alkylation of compounds of the formula I-A or I-D wherein X is NH with a compound of the formula $R^4L$ wherein L is a leaving group, as defined above, or wherein $R^4L$ is $(C_1-C_4)_2SO_2$, in the presence of a base that is capable of deprotonating NH such as sodium hydride or butyllithium, yields the corresponding alkylated derivative of the formula I-B or I-E, respectively. Compounds of formulas IV-A, IV-B, IV-C, IV-D and IV-E wherein M Is T may be converted to the corresponding compounds of formulas I-A through I-E wherein M is $ZR^5$ by the methods described above for converting compounds of the formula IV into compounds of the formulas I, II and III.

Compounds of the formula I-F may be prepared, as illustrated in Scheme 2, by reacting the corresponding compounds of the formula VI-B (wherein M, X, A, B, and $R^{19}$ are defined as in the preceding paragraph) with a base that is capable of deprotonating NH (such as sodium hydride, potassium hydride, or an organometallic base such as lithium diisopropylamide, lithium bis(trimethylsilyl)amide or sodium diisopropylamide) in an appropriate solvent, e.g., a solvent selected from THF, dioxane, DMSO, benzene, toluene, methylene chloride and chloroform. Alternatively, heating a compound of the formula VI-B in the presence of an acid (e.g., p-toluenesulfonic acid, aqueous phosphoric acid concentrated sulfuric acid or gaseous hydrogen chloride), in an appropriate solvent such as toluene, benzene or xylene, will yield the corresponding compound of formula I-F. Alkylation of compounds of formula I-F with a compound of the formula $R^4L$, defined as above, in the presence of a base such as sodium hydride, potassium hydride, or an organometallic base such as lithium diisopropylamide, lithium bis(trimethylsilyl)amide or sodium diisopropylamide, in an appropriate solvent such as THF or dioxane, yields the corresponding compounds of formula I-H.

Compounds of the formula I-J wherein G is chloro or trifliate may be prepared by heating the corresponding compounds of formula I-H with $POCl_3$, with or without $PCl_5$ or $(Tf)_2O$ (wherein Tf is triflate), respectively. Displacement of the chloro or OTf group of a compound of formula I-G with a nucleophile will yield the corresponding compound of formula I-J wherein G is defined for formula I. Compounds of the formula I-G wherein G is S may be prepared by reacting the corresponding compounds of formula I-F with Lawessen's reagent or $P_4S_{10}$. Compounds of the formula I-J wherein G is H may be prepared by reduction of the corresponding compounds of formula I-F or I-H with lithium aluminum hydride ($LiAlH_4$) or borane methyl sulfide complex ($BH_3.DMS$), followed by acid hydrolysis. Organometallics addition (using, e.g., GU, GMgBr or GMgI), followed by acid hydrolysis, employing methods well known in the art, will provide compounds of formula I-J wherein G is $(C_1-C_4)$ alkyl.

Deprotonation of I-H with a base such as NaH in HMPA, followed by quenching with a $(C_1-C_4$ alkyl$)_2SO_2$— or $C_1-C_4$ alkyl containing electrophile, will yield a compound of formula I-J wherein G is O—$(C_1-C_4$ alkyl$)$.

Compounds of formula I-K wherein $R^{22}$ is —OH or —$NH_2$ may be prepared by reacting the corresponding compounds of the formula VI-C with a base or acid as a catalyst to effect ring cyclization as shown in Scheme 3. For example, a base that is capable of deprotonating of the XH of formula VI-C, such as sodium hydride, potassium hydride, or an organometallic base such as lithium diisopropylamide, lithium bis(trimethylsilyl)amide, or sodium diisopropylamide, can be reacted with the appropriate compound of formula VI-C in an appropriate solvent such as THF, dioxane, toluene, DMSO, NMP, a $C_1-C_5$ alcohol or acetonitrile, at temperature from about 0° C. to about 180° C., to effect ring formation. Alternatively, this reaction may be performed by heating the compound of formula VI-C in the presence of an acid catalyst or an appropriate Lewis acid such as aluminium chloride ($AlCl_3$) or borontrifluoride ethyl ether complex ($BF_3.Et_2O$, wherein Et=ethyl).

Conversion of compounds of the formula I-K wherein $R^{22}$ is hydroxy into the corresponding compounds of formula I-L may be accomplished by the method described above for transformation of compounds of the formula I-F into compounds of the formula I-J.

Compounds of the formula I-P may be prepared, as shown in Scheme 4, by reacting compounds of the formula VI-D with sodium nitrite in 48% hydrogen bromide in the presence of cuprous bromide or bromine at a temperature from about 0° C. to about the reflux temperature. Preferably, the reaction is carried out at about 0° C. for about thirty minutes, and then at mild reflux.

As shown in schemes 5 and 6, compounds of the formulas V-M and V-N, wherein Y is N or $C(C_0-C_4)$ alkyl, may be prepared by heating, respectively, compounds of the formula VII and VIII, wherein $R^{23}$ is CN, X is O, S, NH or $N(C_1-C_4$ alkyl), and Y is CH, N or $C(C_1-C_4$ alkyl), with a compound of formula acid $(R^{24}CO)_2O$ in $R^{24}COOH$, at temperature from about 25° C. to about 120° C., preferably at the reflux temperature of the reaction mixture. The above formed compounds wherein $R^{19}$ is hydrogen, $C_1-C_5$ alkyl or hydroxy may be heated in aqueous acid to give compounds of formula V-M or V-N. Appropriate acids include 85% phosphoric acid, hydrochloric acid, sulfuric acid and acetic acid. Eighty-five percent phosphoric acid is preferred. The reaction is carried out at a temperature from about 25° C. to about 180° C., preferably from about 100° C. to about 150° C.

Compounds of the formulas V-M and V-N (wherein Y is N) may be prepared, as shown in Schemes 5 and 6, by heating compounds of the formulas VII and VIII, respectively, [wherein $R^{23}$ is $CONH_2$ or $COO(C_1-C_4$ alkyl), X is O, S, NH or $N(C_1-C_4$ alkyl) and Y is CH or $C(C_1-C_4$ alkyl)], with a compound of the formula $C_{19}CONH_2$ wherein $R^{19}$ is as defined above. This reaction can be conveniently carried out in the absence of a solvent at temperatures ranging from about 100° C. to about 250° C.

Compounds of formula IV-O may be prepared by reacting the corresponding compounds of formula IX wherein A, T, $R^{19}$ and $R^4$ are defined as above with $BNHNH_2$ in an appropriate solvent as shown in Scheme 7. Suitable solvents include $C_1-C_5$ alcohols, acetonitrile, toluene, chlorobenzene, xylene, toluene, dioxane, chloroform and methylene chloride, preferably in i-propanol or acetonitrile.

Compounds of the formula I-Q can be prepared as illustrated In Scheme 8. Compounds of formula XI wherein B is $CR^1R^2R^{10}$ or CN, X is O, S, NH, $N(C_1-C_4$ alkyl), and $R^{10}$, A, Z, $R^5$ are defined as above may be prepared by reacting compounds of formula X with hydroxylamine.HCl in a mixture of a solvent selected from $C_1-C_5$ alcohols, $CH_3CN$, acetone, dioxane and water, with or without sodium acetate, at a temperature from about room temperature to about 120° C., preferably at about the reflux temperature. Compounds of formula XI can then be reacted with an appropriate agent convert the hydroxy group of the oxime into a good leaving group such as —OAc, —$OCOCF_3$, —$OSO_2CF_3$, —$OSO_2CH_3$ or —$OSO_2C_6H_5CH_3$ (p-tosylate). Examples of such appropriate agents are acetic anhydride, trifluoroacetic anhydride, triflic anhydride, methanesulfonyl chloride and p-toluenesulfonyl chloride. This reaction is generally conducted in an appropriate solvent such as methylene chloride, chloroform, acetonitrile, acetone, THF or pyridine, with or without a base such as N,N-dimethylpyridine or a tri-($C_1$–$C_8$ alkyl) amine, at temperature from about 0° C. to about 120° C., preferably from about room temperature to about 80° C. Most preferably, an excess of acetic anhydride is used at a temperature between 80° C. and the reflux temperature. The resulting compounds can then be heated in an appropriate solvent such as DMF, DMSO, sulfolane, dioxane, THF or NMP in the presence of base such as pyridine, a tri($C_1$–$C_4$ alkyl) amine or sodium hydride, at temperature from about 0° C. to about 180° C., preferably from about room temperature to about 150° C., to give the final cyclized compounds of formula I-Q.

Compounds of formula I-Q wherein B is —CN can be converted into the corresponding compounds wherein B is $NR^1R^2$ or $NHCR^1R^2R^{10}$ using a Curtius rearrangement reaction, as described below. Compounds of formula I-Q wherein B is CN are subjected to acid hydrolysis with, e.g., aqueous phosphoric acid, at a temperature between about 80° C. and about 150° C., to yield the corresponding compounds wherein B is COOH. Compounds of the formula I-Q wherein B is COOH can be converted into the corresponding compounds wherein B is —$NH_2$ by reacting them with diphenylphosphorylazide in t-butyl alcohol in the presence of a tri($C_1$–$C_4$ alkyl) amine, followed by acid hydrolysis using, e.g., trifluoroacetic acid, according to procedures well known in the art. The amino derivatives so formed can be converted, also using standard methods well known in the art, into the corresponding compounds wherein B is $NR^1R^2R^{10}$ via an alkylation or reduction amination reaction. Such a procedure is described above for forming compounds of the formula IB.

Reaction of compounds of formula I-Q wherein B is CN with a Grignard reagent (e.g., $R^2MgX'$ wherein X' is halo) at a temperature from about 0° C. to about room temperature in THF, ether or dioxane, followed by quenching with an acid, using the conditions well known in the art, will afford the corresponding ketones of formula I-Q wherein B Is $COR^2$. Reduction of such ketones with sodium borohydride in a $C_1$–$C_5$ alkyl alcohol will afford the corresponding compounds of formula I-Q wherein B is $CHR^2OH$. Alkylation of compounds of formula I-Q wherein B is $CHR^2OH$ with $R^1$-L (wherein L is a leaving group such as halo, mesylate or tosylate) in the presence of a base such as sodium hydride or potassium hydride will yield the corresponding compounds wherein B is $CHR^1R^2$. This reaction is typically carried in an appropriate solvent, e.g., THF, dioxane, ether, toluene or DMSO, at temperature between about 0° C. and about 100° C., preferably between about 0° C. and about room temperature.

The starting materials and intermediates of formulas IV, V, VI, VII, VIII, IX and X are commercially available, known in the art, or able to be synthesized using the procedures disclosed in PCT Patent Application PCT/IB95/00439, PCT Patent Application PCT/IB95/00373, U.S. patent application Ser. No. 08/481,413, U.S. patent application Ser. No. 08/448,539, and U.S. patent application Ser. No. 08/254,820, all of which are referred to and incorporated herein by reference in their entireties above.

In each of the above reactions, pressure is not critical. Pressures in the range of about 0.5–20 atm (0.5–20 bars) are suitable, and ambient pressure (generally, about one atmosphere) is preferred as a matter of convenience. Also, for those reactions where the preferred temperature varies with the particular compounds reacted, no preferred temperature is stated. For such reactions, preferred temperatures for particular reactants may be determined by monitoring the reaction using thin layer chromatography or gas chromatography/mass spectroscopy.

The preparation of other compounds of the formula I not specifically described in the foregoing experimental section can be accomplished using combinations or variations of the reactions described above that will be apparent to those skilled in the art.

Compounds of the formulas I, II and III that are basic in nature are capable of forming a wide variety of different salts with various inorganic and organic acids. Although such salts must be pharmaceutically acceptable for administration to animals, it is often desirable in practice to initially isolate a compound of the formulas I, II or III from the reaction mixture as a pharmaceutically unacceptable salt and then simply convert the latter back to the free base compound by treatment with an alkaline reagent, and subsequently convert the latter free base to a pharmaceutically acceptable acid addition salt. The acid addition salts of compounds of the formulas I, II and III can be prepared in a conventional manner by treating a solution or suspension of the corresponding free base with one chemical equivalent of a pharmaceutically acceptable acid. Conventional concentration or crystallization techniques can be employed to isolate the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzene sulfonic, p-toluenesulfonic, and related acids.

Compounds of the formulas I, II and III that are also acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of formula I. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The active compounds of this invention may be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining the novel compounds of formulas I, II and III and their pharmaceutically acceptable carriers can then be readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, methylcellulose, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions containing an active compound of this invention or a pharmaceutically acceptable salt thereof in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

The effective dosages for compounds of the formulas I, II or III and their salts will depend on the intended route of administration and factors such as the age and weight of the patient, as generally known to a physician. The dosages will also depend on the particular illness to be treated. For instance, the daily dosage for stress-induced illnesses, inflammatory disorders, Alzheimer's disease, gastro-intestinal diseases, anorexia nervosa, hemorrhagic stress and drug and alcohol withdrawal symptoms will generally range from about 0.1 to about 50 mg/kg body weight of the patient to be treated.

Methods that may be used to determine the CRF antagonist activity of the active compounds of this invention and their pharmaceutically acceptable salts are described in *Endocrinology*, 116, 1653–1659 (1985) and *Peptides*, 10, 179–188 (1985). The binding activities for compounds of formulas I, II and III, expressed as $IC_{50}$ values, generally range from about 0.5 nanomolar to about 10 micromolar.

The present invention is illustrated by the following examples. It will be understood, however, that the invention is not limited to the specific details of these examples. Melting points are uncorrected. Proton nuclear magnetic resonance spectra ($^1$H NMR) and $C^{13}$ nuclear magnetic resonance spectra ($C^{13}$ NMR) were measured for solutions in deuterochloroform ($CDCl_3$) and peak positions are expressed in parts per million (ppm) downfield from tetramethylsilane (TMS). The peak shapes are denoted as follows: s, singlet; d, doublet; t, triplet; q, quartet; m, multiplet; b, broad.

The following abbreviations are used in the Examples: Ph=phenyl; iPr=isopropyl; HRMS=high resolution mass spectrum.

EXAMPLE 1

2,5,6-Trimethyl7-(1 propylbutyl)-4-(2,4,6-trimethylphenoxy)-7H-pyrrolo[2,3-d]pyrimidine To a solution of 2,4,6-trimethylphenol (111 mg, 0.82 mmol) in 3 ml of DMSO was added 60% sodium hydride (NaH) in oil (32 mg, 0.8 mmol). After stirring for 10 min, 4-chloro-2,5,6-trimethyl-7-(1-propylbutyl)-7H-pyrrolo[2,3,-d]pyrimidine (200 mg, 0.68 mmol) was added. The resulting mixture was heated at 135° C. in an oil bath for 3 hours. An additional 10 mg of 60% NaH was added and the mixture was heated at 135° C. for an additional 1 hour and cooled to room temperature. The mixture was quenched with water and extracted with ethyl acetate (EtOAc). The organic layer was washed with 2N sodium hydroxide (NaOH) and brine, and then dried and concentrated to give a brown oil. The oil was purified through silica gel column chromatography using chloroform ($CHCl_3$):hexane=4:1 as eluent to give the title compound (79%) as a light green oil. $^1$H NMR ($CDCl_3$) δ 6.92 (s, 2H), 2.43 (s, 3H), 2.42 (s, 3H), 2.33 (s, 6H), 2.12 (s, 6H), 1.7–1.9 (m, 3H), 0.95–1.35 (m, 6H), 0.88 (s, 6H) ppm. MS: [P+]=393 (100%). The corresponding HCl salt was also prepared.

EXAMPLE 2

1-(1-Ethylpropyl)-6-methyl-4-(2,4,6-trimethylphenylamino)-1,3-dihydro-imidazo[4,5-c]pyridin-2-one To a solution of N4-(1-ethylpropyl)-6-methyl-N-2-(2,4,6-trimethylphenyl)-pyridine-2,3,4-triamine (250 mg, 0.77 mmol) in 5 ml of dry tetrahydrofuran (THF) was treated with triphosgene (89 mg, 0.3 mmol) and triethylamine (189 mg, 1.87 mmol) at 0° C. and stirred at room temperature for 0.5 hours. The mixture was quenched with water and extracted with ethyl acetate. The organic layer was dried and concentrated to give 260 mg of a tan solid. The residue was purified through silica gel column chromatography to give 200 mg of the title compound (>90% pure) and 60 mg of white crystals of the title compound. Mp 148–150° C. $^1$H NMR ($CDCl_3$) δ6.96 (s, 2H), 6.39 (s, 1H), 6.00 (s, 1H, NH), 5.94 (s, 1H, NH), 4.03 (m, 1H), 2.44 (s, 3H), 2.32 (s, 3H), 2.20 (s, 6H), 1.80–2.05 (m, 4H), 0.82 (t, 6H) ppm.

The following compounds were prepared by a method analogous to that described in Example 2 starting from the appropriate 4-substituted-N-(1-ethyl-propyl)-2-methyl-pyrimidine-5,6-diamineor2-substituted-N-4-(1-ethylpropyl)-6-methyl-pyridine-3,4-diamine and purified from silica gel column chromatography.

EXAMPLE 3

9-(1-Ethylpropyl)-2-methyl-6-(2,4,6-trimethylphenylamino)-7,9-dihydro-purin-8-one $^1$H NMR ($CDCl_3$) δ 6.98 (s, 2H), 6.81 (s, 1H), 5.709 (brs, 1H), 4.14 (m, 1H), 2.44 (s, 3H), 2.33 (s, 3H), 2.20 (s, 6H), 2.0–2.3 (m, 2H), 1.8–2.0 (s, 3H), 0.81 (t, 6H) ppm.

EXAMPLE 4

1-(1-Ethylpropyl)-6-methyl-4-(2,4,6-trimethylphenoxy)-1,3-dihydro-imidazo[4,5-c]pyridin-2-one Mp 235–237° C. Anal. calc'd for $C_{21}H_{27}N_3O_2$ (C,H,N) [Fill in date or Delete]. $^1$H NMR ($CDCl_3$) δ7.02 (s, $_1$H), 6.91

(s, 2H), 6.61 (s, 1H), 4.12 (m, 1H), 2.39 (s, 3H), 2.32 (s, 3H), 2.12 (s, 6H), 1.8–2.1 (m, 4H), 0.87 (t, 6H) ppm.

EXAMPLE 5

1-(1-Ethylpropyl)-6-methyl-4-(2,4,6-trimethylphenoxy)-1H-imidazo[4,5-c]pyridine

A mixture of N4-(1-ethylpropyl)-6-methyl-2-(2,4,6-trimethylphenoxy)-pyridine-3,4-diamine (160 mg, 0.49 mmol), trimethyl orthoformate (62 mg, 0.59 mmol) and paratosylalcohol (p-TsOH) (10 mg) in 20 ml of toluene was heated at reflux under a Dean-Stark trap apparatus for 24 hours. The mixture was quenched with water and extracted with ethyl acetate. The organic layer was dried and concentrated to give the title compound (160 mg, 97%) as a light brown oil. The oil was purified through silica gel column chromatography using 2% methanol (MeOH) in chloroform as eluent to give a tan solid. Mp 127–131° C. $^1$H NMR (CDCl$_3$) δ 7.82 (s, 1H), 6.90 (s, 2H, 6.81) (s, 1H), 4.02 (m, 1H), 2.37 (s, 3H), 2.32 (s, 3H), 2.13 (s, 6H), 1.98 (m, 4H), 0.87 (t, 6H) ppm.

EXAMPLE 6

1-(1-Ethylpropyl)-3,6-dimethyl-4-(2,4,6-trimethylphenoxy)-1,3-dihydro-imidazo[4,5-c]pyridin-2-one A solution of 1-(1-ethylpropyl)-6-methyl-4-(2,4,6-trimethylphenoxy)-1,3-dihydro-imidazo[4,5-c]pyridin-2-one (100 mg, 0.28 mmol) in 5 ml of dry THF was treated with lithium bis(trimethylsilyl)amide (0.31 ml, 1 M in THF, 0.31 mmol) at −78° C. After 20 min, the mixture was quenched with 1 ml of methyl iodide and stirred at room temperature for 1 hour. The mixture was quenched with water and extracted with ethyl acetate. The organic layer was dried and concentrated to give 110 mg of an off-white solid which was recrystallized from isopropyl ether to give white crystals. Mp 152–154° C.; $^1$H NMR (CDCl$_3$) δ 6.91 (s, 2H), 6.57 (s, 1H), 4.18 (m, 1H), 3.73 (s, 3H), 2.32 (s, 3H), 2.27 (s, 3H), 2.12 (s, 6H), 1.9–2.1 (m, 2H), 1.7–1.9 (m, 2H), 0.88 (t, 6H) ppm.

EXAMPLE 7

1-(1-Ethylpropyl)-3,6-dimethyl-4-(2,4,6-trimethylphenylamino)-1,3-dihydro-imidazo[4,5-c]pyridin-2-one The title compound was prepared by a method analogous to that described in Example 6 starting from 1-(1-ethylpropyl)-6-methyl-4-(2,4,6-trimethylphenylamino)-1,3-dihydro-imidazo[4,5-c]pyridin-2-one. $^1$H NMR (CDCl$_3$) δ 6.91 (s, 2H), 6.42 (s, 1H), 5.77 (s, 1H), 4.13 (m, 1H), 3.49 (s, 3H), 2.31 (s, 6H), 2.17 (s, 6H), 1.9–2.2 (m, 2H), 1.7–1.9 (m, 2H), 0.86 (t, 6H) ppm.

EXAMPLE 8

1-(1-Ethyl-propyl)-6-methyl-4-(2,4,6-trimethyl-phenoxy)-1H-[1,2,3]triazolo[4,5-c]pyridine To a solution of 2-(2,4,6-trimethylphenoxy)-N4-(1-ethylpropyl)-6-methyl-pyridine-3,4-diamine (640 mg, 1.95 mmol) and 7 ml of 48% hydrobromic acid was added a solution of sodium nitrite (146 mg, 2.11 mmol) in 2 ml of water dropwise over 5 min at 0° C. The resulting mixture was treated with cuprous bromide Cu(I)Br (145 mg, 1.01 mmol) and then heated at reflux for 15 min. The mixture was cooled to room temperature and diluted with water, basified with ammonium hydroxide and extracted twice with ethyl acetate. The organic layer was dried and concentred to give 710 mg (93% yield) of the title compound as brown crystals, which was further recrystallized from isopropyl ether to give the title compound as golden crystals. $^1$H NMR (CDCl$_3$) δ 6.92(s,2H), 6.84(s,1H), 4.5(m,1H), 2.40(s,3H), 2.32(s,3H), 2.13(s,6H), 2.0–2.4(m,4HO, 0.83(t,6H)ppm.

EXAMPLE 9

7-Bromo-1-(1-ethyl-propyl)-6-methyl-4-(2,4,6-trimethyl-phenoxy)-1H-[1.2.31 triazolo[4,5-c]pyridine A mixture of 2-(2,4,6-trimethylphenoxy)-N-4-(1-ethylpropyl)-6-methyl-pyridine-3,4-diamine (250 mg, 0.763 mmol), n-butyl nitrite (118 mg, 1.15 mmol) and CuBr$_2$ (205 mg, 0.916 mmol) in anhydrous acetonitrile was heated at 65° C. for 2 hours. The mixture was quenched with 16 ml of 2N HCl and extracted 3 times with ethyl acetate. The organic layer was dried and concentrated to give a light brown form (0.310 g). The crude material was purified through silica gel column chromatography using 1:1 chloroform:ethyl acetate as eluent to give 160 mg of 1-(1-ethyl-propyl)-6-methyl-4-(2,4,6-trimethyl-phenoxy)-1H-[1,2,3]triazolo[4,5-c]pyridine and 60 mg of 7-bromo-1-(1-ethyl-propyl)-6-methyl-4-(2,4,6-trimethyl-phenoxy)-1H-[1,2,3]triazolo [4,5-c]pyridine. Mp 154–156° C.; $^1$H NMR (CDCl$_3$) δ 6.92(s,2H), 5.5(m,1H), 2.51(s,3H), 2.33(s,3H), 2.13(s,6H), 2.2–2.45(m, 2H), 2.0–2.2 (m,2H), 0.87(t,6H) ppm.

EXAMPLE 10

1-(1-Ethyl-propyl)-6,7-dimethyl-4-(2,4,6-trimethylphenoxy)-1H-[1,2,3]triazolo[4,5-c]pyridine To a −78° C. solution of 7-bromo-1-(1-ethyl-propyl)-6-methyl-4-(2,4,6-trimethyl-phenoxy)-1H-[1,2,3]triazolo[4,5-c]pyridine (33 mg, 0.079 mmol) in 2 ml of dry THF was added 2.5 M nBuLi in hexane (0.047 ml, 0.019 mmol) and stirred at that temperature for 5 min. An excess of MeI (0.5 ml) was added and the mixture was stirred at that temperature for 15 min, then gradually warmed to room temperature for 1 hour. The mixture was quenched with saturated ammonium chloride and extracted with ethyl acetate. The organic layer was dried and concentrated to give 31 mg of a golden oil. The oil was purified through silica gel column chromatography using 5% ethyl acetate in hexane as eluent to give the title compound as white crystals. Mp 127–129° C.; $^1$H NMR (CDCl$_3$) δ 6.91 (s,2H), 4.83(m,1H), 2.51(s,3H), 2.38 (s,3H), 2.33(s,3H), 2.13(s,6H), 2.3–2.5(m,2H), 1.9–2.2(m, 2H), 0.86(t,6H) ppm.

EXAMPLE 11

1-(1-Ethyl-propyl)-6-methyl-4-(2,4,6-trimethyl-phenoxy)-1,3-dihydro-pyrrolo [3,2-c]-pyridin-2-one A mixture of [4-(1-ethyl-propylamino)-6-methyl-2-(2,4, 6-trimethyl-phenoxy)-pyridin-3-yl]-acetonitrile (800 mg, 2.27 mmol), 6 ml of 85% phosphoric acid and 2 ml of water was heated at reflux for 2 hours and cooled to room temperature. The reaction mixture was neutralized with 2N NaOH and extracted twice with chloroform. The chloroform layer was dried and concentrated to give a yellow solid. The solid was purified through silica gel column chromatography using hexane to 6% ethyl acetate in hexane as eluent to give 730 mg (92.2%) of a white solid. $^1$H NMR (CDCl$_3$) δ 6.87(s,2H), 6.5(s,1H), 4.1(m,1H), 3.12(s,2H), 2.38(s,3H), 2.30(s,3H), 2.10(s,3H), 1.7–2.0(m,4H), 0.8(t,6H) ppm.

EXAMPLE 12

1-(1-Ethyl-propyl)-6-methyl-(2,4,6-trimethylphenoxy)-1 H-pyrrolo[3,2-c]pyridine

A mixture of 1-(1-Ethyl-propyl)-6-methyl-4-(2,4,6-trimethyl-phenoxy)-1,3-dihydro-pyrrolo[3,2-c]pyridin-2-one (12 mg, 0.034 mmol) and 2M BH$_3$-DMS complex in THF (0.1 ml, 0.2 mmol) in 1 ml of dry THF was heated at reflux for 3 hours. The mixture was quenched with dilute HCl and stirred for 1 hour, then neutralized, and extracted with ethyl acetate. The organic layer was dried and concentrated. The residue was purified through silica gel column chromatography using hexane to 4% ethyl acetate in hexane as eluent to give 6 mg of the title compound. $^1$H NMR (CDCl$_3$) δ 6.88(s,2H), 6.84(s,1H), 6.74(s,1H), 5.97(s,1H), 4.00(m,1H), 2,43(s,3H), 2.30(s,3H), 2.10(s,6H), 1.7–1.9(m,4H), 0.75(t, 6H) ppm.

EXAMPLE 13

1-(1-Ethyl-propyl)-6-methyl-4-(2,4,6-trimethyl-phenoxy)-2,3-dihydro-1H-pyrrolo[3,2-c]pyridine A mixture of 1-(1-Ethyl-propyl)-6-methyl (2,4,6-trimethyl-phenoxy)-1,3-dihydro-pyrrolo[3,2-c]pyridin-2-one (49 mg, 0.142 mmol) and 2M BH$_3$-DMS complex in THF (0.5 ml, 1.0 mmol) in 1 ml of dry THF was heated at reflux for 3 hours. The mixture was quenched with dilute HCl and stirred for 48 hours, then neutralized, and extracted with ethyl acetate. The organic layer was dried and concentrated. The residue was purified through silica gel column chromatography using hexane to 20% ethyl acetate in hexane as eluent to give 15 mg (31%) of the title compound as a clear oil and 18 mg (38%) of 1-(1-Ethyl-propyl)-6-methyl-4-(2, 4,6-trimethyl-phenoxy)-1 H-pyrrolo[3,2-c]pyridine. $^1$H NMR (CDCl$_3$) of the title compound: δ 6.84(s,2H), 5.89(s, 1H), 3.3(t,2H), 3,2(m,1H), 2.5(t,2H), 2.28(s,6H), 2.14(s, 6H), 1.4–1.6(m,4H), 0.88(t,6H)ppm.

EXAMPLE 14

1-(1-Ethyl-propyl)-6-methyl-4-(2,4,6-trimethyl-phenoxy)-1H-imidazo[4,5-c]pyridin-2-ylamine A mixture of of 2-(2,4,6-trimethylphenoxy)-N-4-(1-ethylpropyl)-6-methyl-pyridine-3,4-diamine (200 mg, 0.611 mmol) and 5M BrCN in acetonitrile (0.12 ml, 0.611 mmol) in 3 ml of anhydrous acetonitrile was stirred at room temperature overnight. The mixture was quenched with water and saturated sodium bicarbonate and extracted 3 times with ethyl acetate. The organic extracts was washed with brine, dried and concentrated to give 240 mg of a light green form. The residue was purified through silica gel column chromatography using 10% methanol in chloroform as eluent to give 146 mg (68%) of the title compound as a tan solid. Mp 208–210° C. $^1$H NMR (CDCl$_3$) δ 6.89 (s,2H), 6.68(s,1H), 5.03(s,2H), 3.84(m,1H), 2.31(s,6H), 2.13(s,6H), 1.8–2.2(m,4H), 0.89(t,6H) ppm.

EXAMPLE 15

1-(1-Ethyl-propyl)-3,6-dimethyl-4-(2,4,6-trimethyl-phenoxy)-1,3-dihydro-pyrrolo[3,2-c]pyridin-2-one To a −78° C. solution of 1-(1-ethyl-propyl)-6-methyl-4-(2,4,6-trimethyl-phenoxy)-1,3-dihydro-pyrrolo[3,2-c]pyridin-2-one (352 mg, 1.0 mmol) in 2 ml of dry THF was added 2.5M BuLi in hexane (0.4 mmol, 1.0 mmol). The resulting mixture was stirred at −78° C. for 30 min, then transferred to a −78° C. solution of methyl iodide (3 ml) in 3 ml of dry THF. The resulting mixture was stirred at −78° C. for 1 hour, quenched with saturated ammonium chloride, extracted with ethyl acetate. The organic layer was dried and concentrated to give a clear oil which was purified through silica gel column chromatography using hexane to 10% ethyl acetate in hexane as eluent to give the title compound as tan solid 214 mg (68%). $^1$H NMR (CDCl$_3$) δ 6.88 (s,2H), 6.47(s,1H), 4.1(m,1H), 3.56(q,1H), 2.30(s,3H), 2.26(s,3H), 2.07(s,6H), 1.7–2.0(m,4H), 1.60(d,3H), 0.86(t,6H) ppm.

EXAMPLE 16

1-(1-Ethyl-propyl-3,3,6-trimethyl-4-(2,4,6-trimethyl-phenoxy)-1,3-dihydro-pyrrolo[3,2-c]pyridin-2-one The title compound was prepared by the method analogous to that described in the Example 15 starting from 1 equivalent of 1-(1-ethyl-propyl)-6-methyl-4-(2,4,6-trimethyl-phenoxy)-1,3-dihydro-pyrrolo[3,2-c]pyridin-2-one and 2.5 equivalent of n-BuLi at −78° C., followed by quenching with excess of methyl iodide. $^1$H NMR (CDCl$_3$) δ 6.88(s,2H), 6.46(s,1H), 4.11(m,1H), 2.29(s,3H), 2.24(s, 3H), 2.05(s,6H), 1.8–2.0(m,2H), 1.6–1.8(m,2H), 1.52(s,6H), 0.85(t,6H) ppm.

EXAMPLE 17

1-(1-Ethyl-propyl)-3,3,6-trimethyl (2,4,6-trimethyl-phenoxy)-2,3-dihydro-1H-pyrrolo[3,2-c]pyridine To a solution of 1-(1-ethyl-propyl)-3,3,6-trimethyl-4-(2, 4,6-trimethylphenoxy)-1,3-dihydro-pyrrolo[3,2-c]pyridin-2-one (50 mg) in 2 ml of dry THF was added excess of 2M borane-dimethyl sulfide complex in THF. The resulting mixture was heated at reflux for 6 hours. The mixture was quenched with dilute HCl and stirred for 30 min, neutralized with 2N NaOH, brine and extracted with ethyl acetate. The organic layer was dried and concentrated to give the solid. The solid was purified through silica gel column chromatography using 10% ethyl acetate in chloroform as eluent to give the title compound as a white solid. $^1$H NMR (CDCl$_3$) δ 6.86(s,2H), 5.88(s,1H), 3.3(m,1H), 3,2(s,2H), 2.29(s,3H), 2.13(s,3H), 2.09(s,6H), 1.6(m,4H), 1.47(s,6H), 0.91(t,6H) ppm.

EXAMPLE 18

1-(1-Ethyl-propyl)-3,6-dimethyl-4-(2,4,6-trhnethyl-phenoxy]-1H-pyrrolo [3,2-c]pyridine A mixture of 1-(1-ethyl-propyl)-3,6-dimethyl-4-(2,4,6-trimethyl-phenoxy)-1,3-dihydro-pyrrolo[3,2-c]pyridin-2-one (20 mg, 0.0546 mmol) and 2M borane-dimethyl sulfide complex in THF (0.07 ml) in 1 ml of THF was heated at reflux for 2 hours. The mixture was quenched with dilute HCl and stirred for 30 min, then neutralized and extracted with ethyl acetate. The organic layer was dried and concentrated to give the crude residue. The residue was purified through silic gel column chromatography using hexane to 10% ethyl acetate in hexane as eluent to give the title compound as a white solid. $^1$H NMR (CDCl$_3$) δ 6.89(s,2H), 6.69(s,1H), 6.63(s,1H), 3.92(m,1H), 2,49(s,3H), 2.30(s,3H), 2.11(s,6H), 1.7–1.9(m,4H), 0.78(t,6H)ppm.

EXAMPLE 19

1-(1-Ethyl-propyl)-2-methoxy-3,6-dimethyl-4-(2,4,6-trimethyl-phenoxy)-1H-pyrrolo[3,2-c]pyridine To a 0° C. solution of 1-(1-Ethyl-propyl)-6-methyl-4-(2,4,6-trimethyl-phenoxy)-1,3-dihydro-pyrrolo[3,2-c]pyridin-2-one (134 mg, 0.381 mmol) in 2 ml of HMPA was added 60% sodium hydride in oil (20 mg, 0.5 mmol) and the resulting mixture was stirred at 0° C. for 10 min. Dimethyl sulfate (66.5 mg, 0.53 mmol) was added and stirred for 30 min. The reaction mixture was quenched with dilute acid to pH4 and extracted with ethyl acetate. The organic layer was washed with brine, dried and concentrated to give a clear oil. The oil was purified through silica gel column chromatography using 3% ethyl acetate in hexane as eluent to give 70 mg of the title compound as white solid. $^1$H NMR (CDCl$_3$) δ 6.88(s,2H), 6.61(s,1H), 4.0(m,1H), 3.95(s,3H), 2,44(s, 3H), 2.29(s,3H), 2.26(s,3H), 2.10(s,6H), 1.95–2.1(m,2H), 1.7–1.9(m,2H), 0.78(t,6H)ppm.

EXAMPLE 20

[1-(1-Ethyl-propyl)-6-methyl-1H-[1,2,3]triazolo[4,5-c]pyridin-4-yl]-(2,4,6-trimethyl-phenyl)-amine A mixture of N4-(1-ethyl-propyl)-6-methyl-N-2-(2,4,6-trimethyl-phenyl)pyridine-2,3,4-triamine (250 mg, 0.766 mmol) and butyl nitrite (119 mg, 1.15 mmol) in 16 ml of acetonitrile was heated at 65° C. for 2 hours. The mixture was quenched with 2N HCl, then neutralized to pH 7 and extracted with ethyl acetate. The organic layer was washed with brine, dried and concentrated to give 250 mg of a golden brown residue. tlc indicated two components were obtained from this reaction, in which the more polar one is the title compound. The title compound was isolated as a white crystals, mp 140–142° C., after silica gel column chromatography using 10% ethyl acetate in hexane as eluent. $^1$H NMR (CDCl$^3$) δ 6.94(s,2H), 6.49(s,1H), 4.40(m, 1H), 2.38(s,3H), 2.31(s,3H), 2.23(s,6H), 2.05–2.2(m,2H), 1.9–2.05(m,2H), 0.80(t,6H) ppm.

EXAMPLE 21

4-(4-Bromo-2,6-dimethyl-phenoxy)-1-(1-ethyl-propyl)-6-methyl-1H-oxazolo[5,4-c]pyridin-2-one To a 0° C. solution of 4-(1-ethyl-propylamino)-6-methyl-2-(4-bromo-2,6-dimethyl-phenoxy)-pyridin-3-ol (40 mg, 0.101 mmol) was added triphosgene (10 mg, 0.035 mmol) and triethylamine (7 mg, 0.07 mmol) in 1 ml of dry THF. The resulting mixture was stirred overnight. The mixture was quenched with water and extracted with ethyl acetate. The organic layer was washed with brine, dried and concentrated. The residue was purified through silica gel column chromatography to give 26 mg (61%) of the title compound as a white solid. $^1$H NMR (CDCl$_3$) δ 7.22(s,2H), 6.60(s,1H), 4.02(m,1H), 2.31(s,3H), 2.12(s,6H), 1.8–2.2(m, 4H), 0.94(t,6H)ppm.

EXAMPLE 22

1-(1-Ethyl-propyl)-6-methyl-4-(2,4,6-trimethyl-phenoxy)-1H-oxazolo[5,4-c]pyridin-2-one The title compound was prepared as a grey solid by the method analogous to that described in the Example 21 starting from 4-(1-Ethyl-propylamino)-6-methyl-2-(2,4,6-trimethyl-phenoxy)-pyridin-3-ol and triphosgene. $^1$H NMR (CDCl$_3$) δ 6.87(s,2H), 6.55(s,1H), 3.98(m,1H), 2.29(s,3H), 2.28(s,3H), 2.09(s,6H), 1.9–2.05(m,2H), 1.8–1.9(m,2H), 0.90(t,6H) ppm.

EXAMPLES 23(a)–23(g)

The following compounds can be prepared by the method analogous to that described in Example 11 starting from [4-(1-ethyl-propylamino)-6-methyl-2-(substituted-phenoxy)-pyridin-3-yl]-acetonitrile and phosphoric acid.
(a) 1-(1-Ethyl-propyl)-6-methyl-4-(4-chloro-2,6-dimethyl-phenoxy)-1,3-dihydro-pyrrolo[3,2-c]pyridin-2-one;
(b) 1-(1-Ethyl-propyl)-6-methyl-4-(4-bromo-2,6-dimethyl-phenoxy)-1,3-dihydro-pyrrolo[3,2-c]pyridin-2-one;
(c) 1-(1-Ethyl-propyl)-6-methyl-4-(2-bromo-4-i-propyl-phenoxy)-1,3-dihydro-pyrrolo[3,2-c]pyridin-2-one;
(d) 1-(1-Ethyl-propyl)-6-methyl-4-(2,4-dimethyl-phenoxy)-1,3-dihydro-pyrrolo[3,2-c]pyridin-2-one;
(e) 1-(1-Ethyl-propyl)-6-methyl-4-(4-i-propyl-2,6-dimethyl-phenoxy)-1,3-dihydro-pyrrolo[3,2-c]pydridin-2-one;
(f) 1-(1-Ethyl-propyl)-6-methyl-4-(4 t-butyl-2,6-dimethyl-phenoxy)-1,3-dyhydro-pyrrolo[3,2-c]pyridin-2-one; and
(g) 1-(1-Ethyl-propyl)-6-methyl-4-(4-trifluoromethyl-2,6-dimethyl-phenoxy)-1,3-dihydro-pyrrolo[3,2-c]pyridin-2-one.

EXAMPLES 24(a)–24(j)

The following compounds can be prepared by the method analogous to that described in Example 15 starting from 1-(1-Ethyl-propyl)-6-methyl-4-(substituted-phenoxy)-1,3-dihydro-pyrrolo[3,2-c]pyridin-2-one and an appropriate base, such as BuLi, lithium diisopropylamide, or lithium bis(trimethylsilyl)amide, followed by quenching with an appropriate electrophile such as methyl iodide or ethyl iodide.
(a) 1-(1-Ethyl-propyl)-3,6-dimethyl-4-(4-chloro-2,6-dimethyl-phenoxy)-1,3-dihydro-pyrrolo[3,2-c]pyridin-2-one;
(b) 1-(1-Ethyl-propyl)-3,6-dimethyl-4-(4-bromo-2,6-dimethyl-phenoxy)-1,3-dihydro-pyrrolo[3,2-c]pyridin-2-one;
(c) 1-(1-Ethyl-propyl]-3,6-dimethyl-4-(2-bromo-4-i-propyl-phenoxy)-1,3-dihydro-pyrrolo[3,2-c]pyridin-2-one;
(d) 1-(1-Ethyl-propyl)-3-ethyl-6-methyl-4-(4-chloro-2,6-dimethyl-phenoxy)-1,3-dihydro-pyrrolo[3,2-c]pyridin-2-one;
(e) 1-(Ethyl-propyl)-3-ethyl-6-methyl-4-(4-bromo-2,6-dimethyl-phenoxy)-1,3-dihydro-pyrrolo[3,2]pyridin-2-one;
(f) 1-(1-Ethyl-propyl-3-ethyl-6-methyl-4-(2-bromo-4-i-propyl-phenoxy)-1,3-dihydro-pyrrolo[3,2-c]pyridin-2-one;
(g) 1-(1-Ethyl-propyl)-3,6-dimethyl-4-(2,4-dimethyl-phenoxy)-1,3-dihydro-pyrrolo[3,2-c]pyridin-2-one;
(h) 1-(1-Ethyl-propyl)-3,6-dimethyl-4-(4-i-propyl-2,6-dimethyl-phenoxy)-1,3-dihydro-pyrrolo[3,2-c]pyridin-2-one;
(i) 1-(1-Ethyl-propyl-3,6-dimethyl-4-(4-t-butyl-2,6-dimethyl-phenoxy)-1,3-dihydro-pyrrolo[3,2-c]pyridin-2-one; and (j) 1-(1-Ethyl-propyl)-3,6-dimethyl-4-(4-trifluoromethyl-2,6-dimethyl-phenoxy)-1,3-dihydro-pyrrolo[3,2-c]pyridin-2-one.

EXAMPLES 25(a)–25(k)

The following compounds can be prepared by the method analogous to that described in Example 18 starting from 1-(1-Ethyl-propyl)-3,6-dimethyl-4-(substituted-phenoxy)-1,3-dihydro-pyrrolo-[3,2-c]pyridin-2-one.
(a) 1-(1-Ethyl-propyl)-3,6-dimethyl-4-(4-chloro-2,6-dimethyl-phenoxy)-1H-pyrrolo[3,2-c]pyridine;
(b) 1-(1-Ethyl-propyl)-3,6-dimethyl-4-(4-bromo-2,6-dimethyl-phenoxy)-1H-pyrrolo[3,2-c]pyridine;
(c) 1-(1-Ethyl-propyl) 3,6-dimethyl-4-(2-bromo-4-i-propyl-phenoxy)-1H-pyrrolo[3,2-c]pyridine:
(d) 1-(1-Ethyl-propyl)-3-ethyl-6-methyl-4-(4-chloro-2,6-dimethyl-phenoxy)-1H-pyrrolo[3,2-c]pyridine;
(e) 1-(1-Ethyl-propyl)-3-ethyl-6-methyl-4-(4-bromo-2,6-dimethyl-phenoxy)-1H-pyrrolo[3,2-c]pyridine;
(f) 1-(1-Ethyl-propyl)-3-ethyl-6-methyl-4-(2-bromo-4-i-propyl-phenoxy)-1H-pyrrolo[3,2-c]pyridine;
(g) 1-(1-Ethyl-propyl-3,6-dimethyl-4-(2-bromo-4-i-propyl-phenoxy)-1H-pyrrolo[3,2-c]pyridine;
(h) 1-(1-Ethyl-propyl)-3,6-dimethyl-4-(2,4-dimethyl-phenoxy)-1H-pyrrolo[3,2-c]pyridine;
(i) 1-(1-Ethyl-propyl)-3,6-dimethyl-4-(4-i-propyl-2,6-dimethyl-phenoxy)-1H-pyrrolo[3,2-c]pyridine;
(j) 1-(1-Ethyl-propyl)-3,6-dimethyl-4-(4-t-butyl-2,6-dimethyl-phenoxy)-1H-pyrrolo-3,2-c]pyridine; and
(k) 1-(1-Ethyl-propyl)-3,6-dimethyl-4-(4-trifluoromethyl-2,6-dimethyl-phenoxy)-1H-pyrrolo[3,2-c]pyridine.

EXAMPLES 26(a)–26(g)

(a) 1-(1-Ethyl-propyl)-3,6-dimethyl-4-(4-ethyl-2,6-dimethyl-phenoxy)-1H-pyrrolo[3,2-c]pyridine To a solution of 2.5 N n-BuLi in hexane in dry THF was added a solution of 1 eq. of 1-(1-ethyl-propyl)-3,6-dimethyl-4-(4-bromo-2,6-dimethyl-phenoxy)-1H-pyrrolo[3,2-c]pyridine in dry THF at −78° C. After stirring at that temperature for 5 min, an appropriate electrophile (e.g., DMF, formaldehyde, or a $C_3$–$C_4$ iodide) was added and the resulting mixture was stirred at −78° C. for 30 min, then at 0° C. for 15 min. The mixture was quenched with saturated ammonium chloride and extracted with ethyl acetate. The organic layer was dried and concentrated to give the title compound after silica gel column chromatography.

The following compounds can also be prepared using the foregoing procedure:
(b) 1-(1-Ethyl-propyl-3,6-dimethyl-4-(4-propyl-2,6-dimethyl-phenoxy)-1H-pyrrolo[3,2-c]pyridine;
(c) 1-(1-Ethyl-propyl)-3,6-dimethyl-4-(4-hydroxymethyl-2,6-dimethyl-phenoxy)-1H-pyrrolo[3,2-c]pyridine;
(d) 1-(1-Ethyl-propyl)-3,6-dimethyl-4-(4-formyl-2,6-dimethyl-phenoxy)-1H-pyrrolo[3,2-c]pyridine;
(e) 1-(1-Ethyl-propyl)-3-ethyl-6-methyl-4-(4-propyl-2,6-dimethyl-phenoxy)-1H-pyrrolo[3,2-c]pyridine;
(f) 1-(1-Ethyl-propyl)-3-ethyl-6-methyl-4-(4-hydroxymethyl-2,6-dimethyl-phenoxy)-1H-pyrrolo[3,2-c]pyridine; and
(g) 1-(1-Ethyl-propyl)-3-ethyl-6-methyl-4-(4-formyl-2,6-dimethyl-phenoxy)-1H-pyrrolo [3,2-c]pyridine.

EXAMPLES 27(a)–27(f)

The following examples can be prepared by a reaction sequence similar to those described in Examples 11, 15 and 18 (sequentially), staring from [4-(1-hydroxymethyl-propylamino)-6-methyl-2-(substituted-phenoxy)-pyridin-3-yl]-acetonitrile.
(a) 2-[4-(4-Chloro-2,6-dimethyl-phenoxy)-3,6-dimethyl-pyrrolo[3,2-c]pyridin-1-yl]-butan-1-ol;
(b) 2-[4-(4-bromo-2,6-dimethyl-phenoxy)-3,6-dimethyl-pyrrolo[3,2-c]pyridin-1-yl]-butan-1-ol;
(c) 2-[4-(4-i-propyl-2,6-dimethyl-phenoxy)-3,6-dimethyl-pyrrolo[3,2-c]pyridin-1-yl]-butan-1-ol;
(d) 2-[4-(4-Ethyl-2,6-dimethyl-phenoxy)-3,6-dimethyl-pyrrolo[3,2-c]pyridin-1-yl-butan-1-ol;
(e) 2-[4-(4-trifluoromethyl-2,6-dimethyl-phenoxy)-3,6-dimethyl-pyrrolo[3,2-c]pyridin-1-yl]-butan-1-ol; and
(f) 2-[4-(2-bromo-4-i-propyl-phenoxy)-3,6-dimethyl-pyrrolo[3,2-c]pyridin-1-yl]-butan-ol.

Preparation A 2,5,6-Trimethyl-7-(1-propylbutyl)-7H-pyrrolo[2,3,-d]pyrimidin-4-ol A mixture of N-[3-cyano-4,5-dimethyl-1-(1-propylbutyl)-1H-pyrrol-2-yl]-acetamide (2.16 g, 7.8 mmol) and 85% phosphoric acid (3.5 ml) was heated at 150° C. for 1 hour. The mixture was quenched with water and extracted with chloroform. The organic layer was dried and concentrated to give the title compound as white solid, $^1$H NMR (CDCl$_3$) δ 12.4 (brs, 1H), 4.7 (brs) and 4.0 (brs, total of 1H), 2,46 (s, 3H), 2.36 (s, 3H), 1.6–2.4 (m, 7H), 1.74 (m, 2H), 0.9–1.4 (m, 4H), 0.85 (t, 6H) ppm.

Preparation B

4-Chloro-2,5,6-trimethyl-7-(1-propylbutyl)-7H-pyrrolo[2,3,-d]pyrimidine

A mixture of 2,5,6-trimethyl-7-(1-propylbutyl)-7H-pyrrolo[2,3,-d]pyrimidin-4-ol (524 mg, 0.19 mmol) and phosphorous oxychloride (5.5 ml) was heated at reflux overnight. The mixture was cooled and poured into ice and extracted with ethyl acetate. The organic layer was neutralized with sat. sodium carbonate and brine, dried and concentrated to give the title compound as green solid (96%) which was purified through silica gel column chromatography using 1:1 hexane: chloroform as eluent to give the title compound as white crystals. $^1$H NMR (CDCl$_3$) δ 2.68 (s, 3H), 2.38 (s, 6H), 2.32 (brs, 3H), 1.65–1.9 (m, 3H), 0.8–1.35 (m, 6H), 0.84 (t, 6H) ppm.

What is claimed is:
1. A compound of the formula

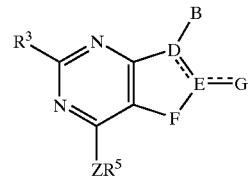

wherein the dashed lines represent optional double bonds;

B is —NR R$^1$R$^2$, —CR$^1$R$^2$R$^{10}$, —C(=CR$^2$R$^{11}$)R$^1$, —NHCR$^1$R$^2$R$^{10}$, —OCR$^1$R$^2$R$^{10}$, —SCR$^1$R$^2$R$^{10}$, CR$^2$R$^{10}$NHR$^1$, —CR$^2$R$^{10}$OR$^1$, —CR$^2$R$^{10}$SR$^1$ or —COR$^2$;

E is nitrogen, CH or carbon;

D is nitrogen and is single bonded to all atoms to which it is attached, or D is carbon and is double bonded to E, or D is CH and is single bonded to E;

F is CHR$^4$ or NR$^4$; provided that either 1) exactly one of D or E is nitrogen and F is CHR$^4$ or 2) F is NR$^4$ and neither D nor E is nitrogen;

G, when single bonded to E is hydrogen, C$_1$–C$_4$ alkyl, —S(C$_1$–C$_4$ alkyl), —O(C$_1$–C$_4$ alkyl), NH$_2$, —NH (C$_1$–C$_4$ alkyl) or —N(C$_1$–C$_2$alkyl)(C$_1$–C$_4$ alkyl) wherein each of the C$_1$–C$_4$ alkyl groups of G may optionally be substituted by one hydroxy, —O(C$_1$–C$_2$ alkyl) or fluoro group; and G when double bonded to E is oxygen, sulfur or NH; and G, when E is nitrogen and double bonded to D, is absent;

R$^1$ is hydrogen, C$_1$–C$_6$ alkyl optionally substituted with one or two substituents R$^8$ independently selected from hydroxy, fluoro, chloro, bromo, iodo, C$_1$–C$_4$ alkoxy, CF$_3$, —C(=O)—(C$_1$–C$_4$)alkyl, —OC(=O)(C$_1$–C$_4$) alkyl, OC(=O)N(C$_1$–C$_4$ alkyl)(C$_1$–C$_2$ alkyl), —NHCO(C$_1$–C$_4$ alkyl), —COOH, —COO(C$_1$–C$_4$ alkyl), —CONH(C$_1$–C$_4$ alkyl), —CON(C$_1$–C$_4$ alkyl) (C$_1$–C$_2$ alkyl), —S(C$_1$–C$_4$ alkyl), —CN, NO$_2$, —SO (C$_1$–C$_4$ alkyl), —SO$_2$(C$_1$–C$_4$ alkyl), —SO$_2$NH(C$_1$–C$_4$ alkyl), SO$_2$N(C$_1$–C$_4$ alkyl)(C$_1$–C$_2$ alkyl), wherein a carbon—carbon single bond of each of the C$_1$–C$_4$ alkyl groups in the foregoing R$^1$ groups having at least two carbons may optionally be replaced with a carbon—carbon double or triple bond, and one or two carbon—carbon single bonds of each of the C$_1$–C$_4$ alkyl groups in the foregoing R$^1$ groups having four carbon atoms may optionally be replaced with a carbon—carbon double or triple bond; R$^2$ is C$_1$–C$_{12}$ alkyl wherein one carbon—carbon single bond of any said alkyl group having at least two carbons, one or two carbon—carbon single bonds of any alkyl having at least four carbons, and from one to three carbon—carbon single bonds of any said alkyl having at least six carbons may optionally be replaced with a carbon—carbon double or triple bond; or R$^2$ is aryl or (C$_1$–C$_4$ alkylene)aryl, wherein said aryl and the aryl moiety of said (C$_1$–C$_4$ alkylene)aryl is selected from phenyl, naphthyl, thienyl, benzothienyl, pyridyl, quinolyl, pyrazinyl, pyrimidinyl, imidazolyl, furanyl, benzofuranyl, benzothiazolyl, isothiazolyl, pyrazolyl, pyrrolyl, indolyl, pyrrolopyridyl, oxazolyl and benzoxazolyl; or R$^2$ is C$_3$–C$_8$ cycloalkyl or (C$_1$–C$_6$ alkylene) (C$_3$–C$_8$ cycloalkyl), wherein one or two of the carbon atoms of said cycloalkyl and the 5 to 8 membered cycloalkyl moieties of said (C$_1$–C$_6$ alkylene)(C$_3$–C$_8$ cycloalkyl) may optionally and independently be replaced by an oxygen or sulfur atom or by NZ$^2$ wherein Z$^2$ is selected from hydrogen, C$_1$–C$_4$ alkyl, benzyl and C$_1$–C$_4$ alkanoyl, and wherein each of the foregoing R$^2$ groups may optionally be substituted with from one to three substituents independently selected from chloro, fluoro, hydroxy and C$_1$–C$_4$ alkyl, or with one substituent selected from bromo, iodo, C$_1$–C$_6$ alkoxy, —OC(=O)(C$_1$–C$_6$ alkyl), OC(=O)N(C$_1$–C$_4$ alkyl)(C$_1$–C$_2$ alkyl), —S(C$_1$–C$_6$ alkyl), amino, —NH (C$_1$–C$_2$ alkyl), —N(C$_1$–C$_2$alkyl)(C$_1$–C$_4$ alkyl), —N(C$_1$–C$_4$ alkyl)—CO—(C$_1$–C$_4$ alkyl), —NHCO (C$_1$–C$_4$ alkyl), —COOH, —COO(C$_1$–C$_4$ alkyl), —CONH(C$_1$–C$_4$ alkyl), CON(C$_1$–C$_4$ alkyl)(C$_1$–C$_2$ alkyl), —SH, —CN, —NO$_2$, —SO(C$_1$–C$_4$ alkyl), —SO$_2$(C$_1$–C$_4$ alkyl), —SO$_2$NH(C$_1$–C$_4$ alkyl) and —SO$_2$N(C$_1$–C$_4$ alkyl)(C$_1$–C$_2$ alkyl);

—NR$^1$R$^2$ may form a 3 to 8 membered ring, said ring consisting of single bonds, wherein, when said ring has from 5 to 8 members, one or two of the ring carbon atoms of such a 5 to 8 membered ring may optionally and independently be replaced by an oxygen or sulfur atom or by NZ$^3$ wherein Z$^3$ is hydrogen, C$_1$–C$_4$ alkyl, benzyl and C$_1$–C$_4$ alkanoyl, and wherein from one to three of the single bonds of such a 3 to 8 membered ring that are carbon—carbon or carbon-nitrogen single bonds may each optionally be replaced by a double bond;

or —CR$^1$R$^2$R$^{10}$ may form a 3 to 8 membered carbocyclic ring, said ring consisting of single bonds, wherein from one to three of the single bonds of such a 3 to 8 membered ring may each optionally be replaced by a double bond;

R$^3$ is hydrogen, C$_1$–C$_4$ alkyl, O(C$_1$–C$_4$ alkyl), chloro, fluoro, bromo, iodo, —CN, —S(C$_1$–C$_4$ alkyl) or —SO$_2$ (C$_1$–C$_4$ alkyl) wherein each of the (C$_1$–C$_4$ alkyl) moieties in the foregoing R$^3$ groups may optionally be substituted with one substituent R$^9$ selected from hydroxy, fluoro and (C$_1$–C$_2$ alkoxy);

each of R$^4$ is, independently hydrogen, (C$_1$–C$_6$ alkyl), fluoro, chloro, bromo, iodo, hydroxy, cyano, amino, nitro, —O(C$_1$–C$_4$ alkyl), N(C$_1$–C$_4$ alkyl)(C$_1$–C$_2$ alkyl), —S(C$_1$–C$_4$ alkyl), —SO(C$_1$–C$_4$ alkyl), —SO$_2$(C$_1$–C$_4$ alkyl), —CO(C$_1$–C$_4$ alkyl), —C(=O)H or C(=O)O (C$_1$–C$_4$ alkyl), wherein one or two of the carbon—carbon single bonds in each of the (C$_1$–C$_6$ alkyl) and (C$_1$–C$_4$ alkyl) moieties in the foregoing R$^4$ groups may optionally be replaced with a carbon—carbon double or triple bond and wherein each of said (C$_1$–C$_6$ alkyl) and (C$_1$–C$_4$ alkyl) moieties may optionally be substituted with one or two substituents independently selected from hydroxy, amino, C$_1$–C$_3$ alkoxy, dimethylamino, methylamino, ethylamino, —NHC(=O)CH$_3$, fluoro, chloro, —CN, —COOH, —C(=O)O(C$_1$–C$_4$ alkyl), —C(=O)(C$_1$–C$_4$ alkyl) and NO$_2$;

R$^5$ is phenyl, naphthyl, thienyl, benzothienyl, pyridyl, quinolyl, pyrazinyl, furanyl, benzofuranyl, benzothiazolyl, benzisothiazolyl, benzisoxazolyl, benzimidazolyl, indolyl, benzoxazolyl or C$_3$–C$_8$ cycloalkyl wherein one or two of the carbon atoms of said cycloalkyl rings that contain at least 5 ring members may optionally and independently be replaced by an oxygen or sulfur atom or by NZ$^4$ wherein N$^4$ is hydrogen, C$_1$–C$_4$ is alkyl or benzyl; and wherein each of the foregoing R$^5$ groups is substituted with from one to four substituents wherein one to three of said substituents may be selected, independently, from chloro, C$_1$–C$_6$ alkyl and —O(C$_1$–C$_6$alkyl) and one of said substituents may be selected from bromo, iodo, formyl, —CN, —CF$_3$, —NO$_2$, —NH$_2$, —NH(C$_1$–C$_4$ alkyl), —N(C$_1$–C$_2$ alkyl)(C$_1$–C$_6$ alkyl), —C(=O)O(C$_1$–C$_4$ alkyl), —C(=O)(C$_1$–C$_4$ alkyl), —COOH, —SO$_2$NH (C$_1$–C$_4$ alkyl), —SO$_2$N(C$_1$–C$_2$ alkyl)(C$_1$–C$_4$ alkyl), —SO$_2$NH$_2$, NHSO$_2$ (C$_1$–C$_4$ alkyl), —S(C$_1$–C$_6$ alkyl) and —SO$_2$ (C$_1$–C$_6$alkyl), and wherein each of the C$_1$–C$_4$ alkyl and C$_1$–C$_6$ alkyl, moieties in the foregoing R$^5$ groups may optionally be substituted with one or two substituents independently selected from fluoro, hydroxy, amino, methylamino, dimethylamino and acetyl; and furthermore wherein when $R^5$ is phenyl or pyridyl substituted with three substituents, said substituents can further be selected from $(C_1-C_4$ alkyl)O $(C_1-C_4$ alkyl), $OCF_3$, and fluoro, and one carbon—carbon single bond of each $(C_1-C_4)$ alkyl group of said substituents having between two and four carbon atoms may be optionally replaced with a carbon—carbon double or triple bond; or $R^5$ is pyrimidyl substituted by three substituents independently selected from $C_1-C_4$ alkyl, —O($C_1-C_4$ alkyl), $CF_3$, $OCF_3$, —CHO, $(C_1-C_4$ alkyl)—OH, CN, Cl, F, Br, I and $NO_2$, wherein a carbon—carbon single bond of said $(C_1-C_4)$ alkyl groups having between two and four carbon atoms may optionally be replaced by a carbon—carbon double or triple bond;

$R^7$ is hydrogen, $C_1-C_4$ alkyl, halo, cyano, hydroxy, O($C_1-C_4$ alkyl)—C(=O)($C_1-C_4$ alkyl), —C(=O)O $(C_1-C_4$ alkyl), —$OCF_3$, —$CF_3$, —$CH_2$—OH, —$CH_2$O $(C_1-C_4$ alkyl);

$R^{10}$ is hydrogen, hydroxy, methoxy or fluoro;

$R^{11}$ is hydrogen or $C_1-C_4$ alkyl; and with the proviso that: (a) when $R^4$ is attached to nitrogen, it not halo, cyano or nitro;

Z is NH, oxygen, sulfur, —N($C_1-C_4$ alkyl), —NC(=O) $(C_1-C_2$ alkyl), NC(=O)O($C_1-C_2$ alkyl) or $CR^{13} R^{14}$ wherein $R^{13}$ and $R^{14}$ are independently selected from hydrogen, trifluoromethyl and methyl with the exception that one of $R^{13}$ and $R^{14}$ can be cyano;

or a pharmaceutically acceptable salt of such compound.

2. A compound according to claim 1 wherein $R^1$ is $C_1-C_6$ alkyl which may optionally be substituted with one hydroxy, fluoro, $CF_3$, or $C_1-C_4$ alkoxy group and may optionally contain one double or triple bond provided that at least two carbons are present in the $C_1-C_6$ alkyl group; and $R^2$ is benzyl, $C_1-C_6$ alkyl, which may optionally contain one double or triple bond provided that at least two carbons are present, where said $C_1-C_6$ alkyl and the phenyl moiety of said benzyl may optionally be substituted with one fluoro $CF_3$, or $C_1-C_2$ alkyl, $C_1-C_2$ alkoxy or chloro group.

3. A compound according to claim 1 wherein: $R^3$ is methyl, ethyl, chloro or methoxy; $R^4$ is methyl or ethyl, G is hydrogen, methyl, ethyl, or E=G is C=O or C=S and $R^5$ is phenyl, pyridyl, or pyrimidyl which is substituted with more than two substituents which are independently selected from $C_1-C_4$ alkyl and —O($C_1-C_4$ alkyl), ($C_1-C_4$ alkyl) —O—($C_1-C_2$ alkyl), $CF_3$, $OCF_3$, —CHO, ($C_1-C_4$alkyl) —OH, CN, Cl, F, Br, I and $NO_2$, wherein one of the carbon—carbon single bonds of each of the foregoing $(C_1-C_4)$alkyl, groups having at least two carbons may optionally be replaced by a carbon—carbon double or triple bond.

4. A compound according to claim 1 wherein E is carbon.

5. A compound according to claim 1 wherein E is nitrogen.

6. A compound according to claim 1 wherein F is $NR^4$.

7. A compound as claimed in claim 1 wherein F is $CHR^4$.

8. A compound of the formula

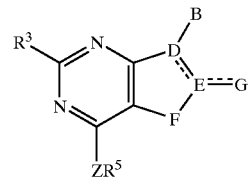

wherein the dashed lines represent optional double bonds;

B is —$NR^1R^2$, —$CR^1R^2R^{10}$, —C(=$CR^2R^{11}$)$R^1$, —$NHCR^1R^2R^{10}$, —$OCR^1R^2R^{10}$, —$SCR^1R^2R^{10}$, $CR^2R^{10}NHR^1$, —$CR^2R^{10}OR^1$, —$CR^2R^{10}SR^1$ or —$COR^2$;

E is nitrogen, CH or carbon;

D is nitrogen and is single bonded to all atoms to which it is attached, or D is carbon and is double bonded to E, or D is CH and is single bonded to E;

F is $CHR^4$ or $NR^4$; provided that either 1) exactly one of D or E is nitrogen and F is $CHR^4$ or 2) F is $NR^4$ and neither D nor E is nitrogen;

G, when single bonded to E is hydrogen, $C_1-C_4$ alkyl, —S($C_1-C_4$ alkyl), —O($C_1-C_4$ alkyl), $NH_2$, —NH $(C_1-C_4$ alkyl) or —N($C_1-C_2$ alkyl)($C_1-C_4$ alkyl) wherein each of the $C_1-C_4$ alkyl groups of G may optionally be substituted by one hydroxy, —O($C_1-C_2$ alkyl) or fluoro group; and G when double bonded to E is oxygen, sulfur or NH; and G, when E is nitrogen and double bonded to D, is absent;

$R^1$ is hydrogen, $C_1-C_6$ alkyl optionally substituted with one or two substituents $R^8$ independently selected from hydroxy, fluoro, chloro, bromo, iodo, $C_1-C_4$ alkoxy, $CF_3$, —C(=O)—(C(=O)O—($C_1-C_4$) alkyl, —OC (=O)($C_1-C_4$) alkyl, OC(=O)N($C_1-C_4$ alkyl)($C_1-C_2$ alkyl), —NHCO($C_1-C_4$ alkyl), —COOH, —COO $(C_1-C_4$ alkyl), —CONH($C_1-C_4$ alkyl), —CON($C_1-C_4$ alkyl)($C_1-C_2$ alkyl), —S($C_1-C_4$ alkyl), —CN, $NO_2$, —SO($C_1-C_4$ alkyl), —$SO_2$($C_1-C_4$ alkyl), —$SO_2$NH $(C_1-C_4$ alkyl), $SO_2$N($C_1-C_4$ alkyl)($C_1-C_2$ alkyl), wherein a carbon—carbon single bond of each of the $C_1-C_4$ alkyl groups in the foregoing $R^1$ groups having at least two carbons may optionally be replaced with a carbon—carbon double or triple bond, and one or two carbon—carbon single bonds of each of the $C_1-C_4$ alkyl groups in the foregoing $R^1$ groups having four carbon atoms may optionally be replaced with a carbon—carbon double or triple bond; $R^2$ is $C_1-C_{12}$ alkyl wherein one carbon—carbon single bond of any said alkyl group having at least two carbons, one or two carbon—carbon single bonds of any alkyl having at least four carbons, and from one to three carbon—carbon single bonds of any said alkyl having at least six carbons may optionally be replaced with a carbon—carbon double or triple bond; or $R^2$ is aryl or $(C_1-C_4$ alkylene)aryl, wherein said aryl and the aryl moiety of said $(C_1-C_4$ alkylene)aryl is selected from phenyl, naphthyl, thienyl, benzothienyl, pyridyl, quinolyl, pyrazinyl, pyrimidinyl, imidazolyl, furanyl, benzofuranyl, benzothiazolyl, isothiazolyl, pyrazolyl, pyrrolyl, indolyl, pyrrolopyridyl, oxazolyl and benzoxazolyl; or $R^2$ is $C_3-C_8$ cycloalkyl or $(C_1-C_6$ alkylene) $(C_3C_8$ cycloalkyl), wherein one or two of the carbon atoms of said cycloalkyl and the 5 to 8 membered cycloalkyl moieties of said $(C_1-C_6$ alkylene)$(C_3-C_8$ cycloalkyl) may optionally and independently be replaced by an oxygen or sulfur atom or by $NZ^2$ wherein $Z^2$ is selected from hydrogen, $C_1-C_4$ alkyl, benzyl and $C_1-C_4$ alkanoyl, and wherein each of the foregoing $R^2$ groups may optionally be substituted with from one to three substituents independently selected from chloro, fluoro, hydroxy and $C_1-C_4$ alkyl, or with one substituent selected from bromo, iodo, $C_1-C_6$ alkoxy, —OC(=O)$(C_1-C_6$ alkyl), OC(=O)N$(C_1-C_4$ alkyl)$(C_1-C_2$ alkyl), —S$(C_1-C_6$ alkyl), amino, —NH $(C_1-C_2$ alkyl), —N$(C_1-C_2$ alkyl)$(C_1-C_4$ alkyl), —N$(C_1-C_4$ alkyl)-CO—$(C_1-C_4$ alkyl), —NHCO $(C_1-C_4$ alkyl), —COOH, —COO$(C_1-C_4$ alkyl), —CONH$(C_1-C_4$ alkyl), CON$(C_1-C_4$ alkyl)$(C_1-C_2$ alkyl), —SH, —CN, —NO$_2$, —SO$(C_1-C_4$ alkyl), —SO$_2(C_1-C_4$ alkyl), —SO$_2$NH$(C_1-C_4$ alkyl) and —SO$_2$N$(C_1-C_4$ alkyl)$(C_1-C_2$ alkyl); —NR$^1$R$^2$ may form a 3 to 8 membered ring, said ring consisting of single bonds, wherein, when said ring has from 5 to 8 members, one or two of the ring carbon atoms of such a 5 to 8 membered ring may optionally and independently be replaced by an oxygen or sulfur atom or by $NZ^3$ wherein $Z^3$ is hydrogen, $C_1-C_4$ alkyl, benzyl and $C_1-C_4$ alkanoyl, and wherein from one to three of the single bonds of such a 3 to 8 membered ring that are carbon—carbon or carbon-nitrogen single bonds may each optionally be replaced by a double bond;

or —CR$^1$R$^2$R$^{10}$ may form a 3 to 8 membered carbocyclic ring, said ring consisting of single bonds, wherein from one to three of the single bonds of such a 3 to 8 membered ring may each optionally be replaced by a double bond;

$R^3$ is hydrogen, $C_1-C_4$ alkyl, O$(C_1-C_4$ alkyl), chloro, fluoro, bromo, iodo, —CN, —S$(C_1-C_4$ alkyl) or —SO$_2$ $(C_1-C_4$ alkyl) wherein each of the $(C_1-C_4$ alkyl) moieties in the foregoing $R^3$ groups may optionally be substituted with one substituent $R^9$ selected from hydroxy, fluoro and $(C_1-C_2$ alkoxy);

each of of $R^4$ is, independently hydrogen, $(C_1-C_6$ alkyl), fluoro, chloro, bromo, iodo, hydroxy, cyano, amino, nitro, —O$(C_1-C_4$ alkyl), N$(C_1-C_4$ alkyl)$(C_1-C_2$ alkyl), —S$(C_1-C_4$ alkyl), —SO$(C_1-C_4$ alkyl), —SO$_2(C_1-C_4$ alkyl), —CO$(C_1-C_4$ alkyl), —C(=O)H or C(=O)O $(C_1-C_4$ alkyl), wherein one or two of the carbon—carbon single bonds in each of the $(C_1-C_6$ alkyl) and $(C_1-C_4$ alkyl) moieties in the foregoing $R^4$ groups may optionally be replaced with a carbon—carbon double or triple bond and wherein each of said $(C_1-C_6$ alkyl) and $(C_1-C_4$ lkyl) moieties may optionally be substituted with one or two substituents independently selected from hydroxy, amino, $C_1-C_3$ alkoxy, dimethylamino, methylamino, ethylamino, —NHC(=O)CH$_3$, fluoro, chloro, —CN, —COOH, —C(=O)O$(C_1-C_4$ alkyl), —C(=O)$(C_1-C_4$ alkyl) and NO$_2$;

$R^5$ is phenyl, naphthyl, thienyl, benzothienyl, pyridyl, quinolyl, pyrazinyl, furanyl, benzofuranyl, benzothiazolyl, benzisothiazolyl, benzisoxazolyl, benzimidazolyl, indolyl, benzoxazolyl or $C_3-C_8$ cycloalkyl wherein one or two of the carbon atoms of said cycloalkyl rings that contain at least 5 ring members may optionally and independently be replaced by an oxygen or sulfur atom or by $NZ^4$ wherein $N^4$ is hydrogen, $C_1-C_4$ is alkyl or benzyl; and wherein each of the foregoing $R^5$ groups is substituted with from one to four substituents wherein one to three of said substituents may be selected, independently, from chloro, $C_1-C_6$ alkyl and —O$(C_1-C_6$ alkyl) and one of said substituents may be selected from bromo, iodo, formyl, —CN, —CF$_3$, —NO$_2$, —NH$_2$, —NH$(C_1-C_4$ alkyl), —N$(C_1-C_2$ alkyl)$(C_1-C_6$ alkyl), —C(=O)O$(C_1-C_4$ alkyl), —C(=O)$(C_1-C_4$ alkyl), —COOH, —SO$_2$NH $(C_1-C_4$ alkyl), —SO$_2$N$(C_1-C_2$ alkyl) $(C_1-C_4$ alkyl), —SO$_2$NH$_2$, NHSO$_2$ $(C_1-C_4$ alkyl), S$(C_1-C_6$ alkyl) and —SO$_2$ $(C_1-C_6$ alkyl), and wherein each of the $C_1-C_4$ alkyl and $C_1-C_6$ alkyl, moieties in the foregoing $R^5$ groups may optionally be substituted with one or two substituents independently selected from fluoro, hydroxy, amino, methylamino, dimethylamino and acetyl;

$R^7$ is hydrogen, $C_1$ $C_4$ alkyl, halo, cyano, hydroxy, —O$(C_1-C_4$ alkyl) —C(=O)$(C_1-C_4$ alkyl), —C(=O) O$(C_1-C_4$ alkyl), —OCF$_3$, —CF$_3$, —CH$_2$—OH, —CH$_2$O$(C_1-C_4$ alkyl);

$R^{10}$ is hydrogen, hydroxy, methoxy or fluoro;

$R^{11}$ is hydrogen or $C_1-C_4$ alkyl; and with the proviso that: (a) when $R^4$ is attached to nitrogen, it not halo, cyano or nitro;

Z is NH, oxygen, sulfur, —N$(C_1-C_4$ alkyl), —NC(=O) $(C_1-C_2$ alkyl), NC(=O)O$(C_1-C_2$ alkyl) or CR$^{13}$R$^{14}$ wherein R$^{13}$ and R$^{14}$ are independently selected from hydrogen, trifluoromethyl and methyl with the exception that one of R$^{13}$ and R$^{14}$ can be cyano;

or a pharmaceutically acceptable salt of such compound.

9. A compound of the formula

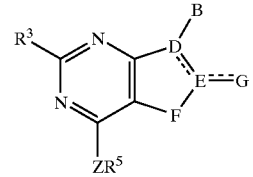

wherein the dashed lines represent optional double bonds;

B is —NR R$^1$R$^3$, —CR$^1$R$^2$R$^{10}$, —C(=CR$^2$R$^{11}$)R$^1$, —NHCR$^1$R$^2$R$^{10}$, —OCR$^1$R$^2$R$^{10}$, —SCR$^1$R$^2$R$^{10}$, CR$^2$R$^{10}$NHR$^1$, —CR$^2$R$^{10}$OR$^1$, —CR$^2$R$^{10}$SR$^1$ or —COR$^2$;

E is nitrogen, CH or carbon;

D is nitrogen and is single bonded to all atoms to which it is attached, or D is carbon and is double bonded to E, or D is CH and is single bonded to E;

F is CHR$^4$ or NR$^4$, provided that either 1) exactly one of D or E is nitrogen and F is CHR$^4$ or 2) F is NR$^4$ and neither D nor E is nitrogen G, when single bonded to E is hydrogen, $C_1-C_4$ alkyl, —S$(C_1-C_4$ alkyl), —O$(C_1-C_4$ alkyl), NH$_2$, —NH $(C_1-C_4$ alkyl) or —N$(C_1-C_2$ alkyl)$(C_1-C_4$ alkyl) wherein each of the $C_1-C_4$ alkyl groups of G may optionally be substituted by one hydroxy, —O$(C_1-C_2$ alkyl) or fluoro group; and G when double bonded to E is oxygen, sulfur or NH; and G, when E is nitrogen and double bonded to D, is absent;

$R^1$ is $C_1-C_6$ alkyl optionally substituted with one substituent selected from hydroxy, fluoro, CF$_3$, or $C_{1-4}$ alkoxy wherein a carbon—carbon single bond of each of the $C_1-C_4$ alkyl groups in the foregoing $R^1$ groups having at least two carbons may optionally be replaced with a carbon—carbon double or triple bond, $R^2$ is benzyl or $C_{1-6}$ alkyl which may optionally contain one double or triple bond and wherein said $C_{1-6}$ alkyl and the phenyl moiety of said benzyl may optionally be substituted with one fluoro, $CF_3$, $C_1$–$C_2$ alkyl $C_1$–$C_2$ alkoxy or chloro group;

—$NR^1R^2$ may form a 3 to 8 membered ring, said ring consisting of single bonds, wherein, when said ring has from 5 to 8 members, one or two of the ring carbon atoms of such a 5 to 8 membered ring may optionally and independently be replaced by an oxygen or sulfur atom or by $NZ^3$ wherein $Z^3$ is hydrogen, $C_1$–$C_4$ alkyl, benzyl and $C_1$–$C_4$ alkanoyl, and wherein from one to three of the single bonds of such a 3 to 8 membered ring that are carbon—carbon or carbon-nitrogen single bonds may each optionally be replaced by a double bond;

or —$CR^1R^2R^{10}$ may form a 3 to 8 membered carbocyclic ring, said ring consisting of single bonds, wherein from one to three of the single bonds of such a 3 to 8 membered ring that are carbon—carbon or carbon-nitrogen single bonds may each optionally be replaced by a double bond;

$R^3$ is hydrogen, $C_1$–$C_4$ alkyl, $O(C_1$–$C_4$ alkyl), chloro, fluoro, bromo, iodo, —CN, —$S(C_1$–$C_4$ alkyl) or —$SO_2(C_1$–$C_4$ alkyl) wherein each of the ($C_1$–$C_4$ alkyl) moieties in the foregoing $R^3$ groups may optionally be substituted with one substituent $R^9$ selected from hydroxy, fluoro and ($C_1$–$C_2$ alkoxy);

each of $R^4$ is, independently hydrogen, ($C_1$–$C_6$ alkyl), fluoro, chloro, bromo, iodo, hydroxy, cyano, amino, nitro, —$O(C_1$–$C_4$ alkyl), $N(C_1$–$C_4$ alkyl)($C_1$–$C_2$ alkyl), —$S(C_1$–$C_4$ alkyl), —$SO(C_1$–$C_4$ alkyl), —$SO_2(C_1$–$C_4$ alkyl), —$CO(C_1$–$C_4$ alkyl), —C(=O)H or C(=O)O ($C_1$–$C_4$ alkyl), wherein one or two of the carbon—carbon single bonds in each of the ($C_1$–$C_6$ alkyl) and ($C_1$–$C_4$ alkyl) moieties in the foregoing $R^4$ groups may optionally be replaced with a carbon—carbon double or triple bond and wherein each of said ($C_1$–$C_6$ alkyl) and ($C_1$–$C_4$ alkyl) moieties may optionally be substituted with one or two substituents independently selected from hydroxy, amino, $C_1$–$C_3$ alkoxy, dimethylamino, methylamino, ethylamino, —$NHC(=O)CH_3$, fluoro, chloro, —CN, —COOH, —C(=O)O($C_1$–$C_4$ alkyl), —C(=O)($C_1$–$C_4$ alkyl) and $NO_2$;

$R^5$ is phenyl, naphthyl, thienyl, benzothienyl, pyridyl, quinolyl, pyrazinyl, furanyl, benzofuranyl, benzothiazolyl, benzisothiazolyl, benzisoxazolyl, benzimidazolyl, indolyl, benzoxazolyl or $C_3$–$C_8$ cycloalkyl wherein one or two of the carbon atoms of said cycloalkyl rings that contain at least 5 ring members may optionally and independently be replaced by an oxygen or sulfur atom or by $NZ^4$ wherein $N^4$ is hydrogen, $C_1$–$C_4$ is alkyl or benzyl; and wherein each of the foregoing $R^5$ groups is substituted with from one to four substituents wherein one to three of said substituents may be selected, independently, from chloro, $C_1$–$C_6$ alkyl and —$O(C_1$–$C_6$ alkyl) and one of said substituents may be selected from bromo, iodo, formyl, —CN, —$CF_3$, —$NO_2$, —$NH_2$—$NH(C_1$–$C_4$ alkyl), —$N(C_1$–$C_2$ alkyl)($C_1$–$C_6$ alkyl), —C(=O)O($C_1$–$C_4$ alkyl), —C(=O)($C_1$–$C_4$ alkyl), —COOH, —$SO_2NH(C_1$–$C_4$ alkyl), —$SO_2N(C_1$–$C_2$ alkyl) ($C_1$–$C_4$ alkyl), —$SO_2NH_2$, $NHSO_2$ ($C_1$–$C_4$ alkyl), —$S(C_1$–$C_6$ alkyl) and —$SO_2$ ($C_1$–$C_6$ alkyl), and wherein each of the $C_1$–$C_4$ alkyl and $C_1$–$C_6$ alkyl, moieties in the foregoing $R^5$ groups may optionally be substituted with one or two substituents independently selected from fluoro, hydroxy, amino, methylamino, dimethylamino and acetyl;

$R^7$ is hydrogen, $C_1$–$C_4$ alkyl, halo, cyano, hydroxy, —$O(C_1$–$C_4$ alkyl) —C(=O)($C_1$–$C_4$ alkyl), —C(=O) $O(C_1$–$C_4$ alkyl), —$OCF_3$, —$CF_3$, —$CH_2$—OH, —$CH_2O(C_1$–$C_4$ alkyl);

$R^{10}$ is hydrogen, hydroxy, methoxy or fluoro;

$R^{11}$ is hydrogen or $C_1$–$C_4$ alkyl; and with the proviso that: (a) when $R^4$ is attached to nitrogen, it not halo, cyano or nitro;

Z is NH, oxygen, sulfur, —$N(C_1$–$C_4$ alkyl), —NC(=O) ($C_1$–$C_2$ alkyl), NC(=O) $O(C_1$–$C_2$ alkyl) or $CR^{13}R^{14}$ wherein $R^{13}$ and $R^{14}$ are independently selected from hydrogen, trifluoromethyl and methyl with the exception that one of $R^{13}$ and $R^{14}$ can be cyano;

or a pharmaceutically acceptable salt of such compound.

10. A compound of the formula

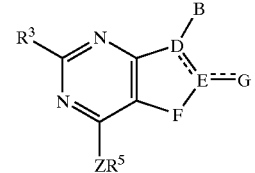

wherein the dashed lines represent optional double bonds;

B is —$NR^1R^2$, —$CR^1R^2R^{10}$, —C(=$CR^2R^{11})R^1$, —$NHCR^1R^2R^{10}$, —$OCR^1R^2R^{10}$, —$SCR^1R^2R^{10}$, $CR^2R^{10}NHR^1$, —$CR^2R^{10}OR^1$, —$CR^2R^{10}SR^1$ or —$COR^2$;

E is nitrogen, CH or carbon;

D is nitrogen and is single bonded to all atoms to which it is attached, or D is carbon and is double bonded to E, or D is CH and is single bonded to E;

F is $CHR^4$ or $NR^4$; provided that either 1) exactly one of D or E is nitrogen and F is $CHR^4$ or 2) F is $NR^4$ and neither D nor E is nitrogen;

G, is hydrogen, methyl or ethyl or E=G is C=O or C=S;

$R^1$ is hydrogen, $C_1$–$C_6$ alkyl optionally substituted with one or two substituents $R^8$ independently selected from hydroxy, fluoro, chloro, bromo, iodo, $C_1$–$C_4$ alkoxy, $CF_3$, —C(=O)O—($C_1$–$C_4$)alkyl, —OC(=O)($C_1$–$C_4$) alkyl, OC(=O)N ($C_1$–$C_4$ alkyl)($C_1$–$C_2$ alkyl), —NHCO($C_1$–$C_4$ alkyl), —COOH, —COO($C_1$–$C_4$ alkyl), —CONH($C_1$–$C_4$ alkyl), —CON($C_1$–$C_4$ alkyl) ($C_1$–$C_2$ alkyl), —$S(C_1$–$C_4$ alkyl), —CN, $NO_2$, —SO ($C_1$–$C_4$ alkyl), —$SO_2(C_1$–$C_4$ alkyl), —$SO_2NH(C_1$–$C_4$ alkyl), $SO_2N(C_1$–$C_4$ alkyl)($C_1$–$C_2$ alkyl), wherein a carbon—carbon single bond of each of the $C_1$–$C_4$ alkyl groups in the foregoing $R^1$ groups having at least two carbons may optionally be replaced with a carbon—carbon double or triple bond, and one or two carbon—carbon single bonds of each of the $C_1$–$C_4$ alkyl groups in the foregoing $R^1$ groups having four carbon atoms may optionally be replaced with a carbon—carbon double or triple bond; $R^2$ is $C_1$–$C_{1-2}$ alkyl wherein one carbon—carbon single bond of any said alkyl group having at least two carbons, one or two carbon—carbon single bonds of any alkyl having at least four carbons, and from one to three carbon—carbon single bonds of any said alkyl having at least six carbons may optionally be replaced with a carbon—carbon double or triple bond; or $R^2$ is aryl or ($C_1$–$C_4$ alkylene)aryl, wherein said aryl and the aryl moiety of said ($C_1$–$C_4$ alkylene)aryl is selected from phenyl, naphthyl, thienyl, benzothienyl, pyridyl, quinolyl, pyrazinyl, pyrimidinyl, imidazolyl, furanyl, benzofuranyl, benzothiazolyl, isothiazolyl, pyrazolyl, pyrrolyl, indolyl, pyrrolopyridyl, oxazolyl and benzoxazolyl; or $R^2$ is $C_3$–$C_8$ cycloalkyl or ($C_1$–$C_6$ alkylene)($C_3$–$C_8$ cycloalkyl), wherein one or two of the carbon atoms of said cycloalkyl and the 5 to 8 membered cycloalkyl moieties of said ($C_1$–$C_6$ alkylene)($C_3$–$C_8$ cycloalkyl) may optionally and independently be replaced by an oxygen or sulfur atom or by $NZ^2$ wherein $Z^2$ is selected from hydrogen, $C_1$–$C_4$ alkyl, benzyl and $C_1$–$C_4$ alkanoyl, and wherein each of the foregoing $R^2$ groups may optionally be substituted with from one to three substituents independently selected from chloro, fluoro, hydroxy and $C_1$–$C_4$ alkyl, or with one substituent selected from bromo, iodo, $C_1$–$C_6$ alkoxy, —OC(=O)($C_1$–$C_6$ alkyl), OC(=O)N($C_1$–$C_4$ alkyl)($C_1$–$C_2$ alkyl), —S($C_1$–$C_6$ alkyl), amino, —NH($C_1$–$C_2$ alkyl), —N($C_1$–$C_2$ alkyl)($C_1$–$C_4$ alkyl), —N($C_1$–$C_4$ alkyl)-CO—($C_1$–$C_4$ alkyl), —NHCO($C_1$–$C_4$ alkyl), —COOH, —COO($C_1$–$C_4$ alkyl), —CONH($C_1$–$C_4$ alkyl), CON($C_1$–$C_4$ alkyl)($C_1$–$C_2$ alkyl), —SH, —CN, —NO$_2$, —SO($C_1$–$C_4$ alkyl), —SO$_2$($C_1$–$C_4$ alkyl), —SO$_2$NH($C_1$–$C_4$ alkyl) and —SO$_2$N($C_1$–$C_4$ alkyl)($C_1$–$C_2$ alkyl);

—$NR^1R^2$ may form a 3 to 8 membered ring, said ring consisting of single bonds, wherein, when said ring has from 5 to 8 members, one or two of the ring carbon atoms of such a 5 to 8 membered ring may optionally and independently be replaced by an oxygen or sulfur atom or by $NZ^3$ wherein $Z^3$ is hydrogen, $C_1$–$C_4$ alkyl, benzyl and $C_1$–$C_4$ alkanoyl, and wherein from one to three of the single bonds of such a 3 to 8 membered ring that are carbon—carbon or carbon-nitrogen single bonds may each optionally be replaced by a double bond;

or —$CR^1R^2R^{10}$ may form a 3 to 8 membered carbocyclic ring, said ring consisting of single bonds, wherein from one to three of the single bonds of such a 3 to 8 membered ring that are carbon—carbon or carbon-nitrogen single bonds may each optionally be replaced by a double bond;

$R^3$ is methyl, ethyl, chloro or methoxy;

each of $R^4$ is methyl, ethyl or trifluoro methyl;

$R^5$ is phenyl or pyridyl, $R^7$ is hydrogen, $C_1$–$C_4$ alkyl, halo, cyano, hydroxy, —O($C_1$–$C_4$ alkyl) —C(=O)($C_1$–$C_4$ alkyl), —C(=O)O($C_1$–$C_4$ alkyl), —OCF$_3$, —CF$_3$, —CH$_2$—OH, —CH$_2$O($C_1$–$C_4$ alkyl);

$R^{10}$ is hydrogen, hydroxy, methoxy or fluoro;

$R_{11}$ is hydrogen or $C_1$–$C_4$ alkyl; and with the proviso that: (a) when $R^4$ is attached to nitrogen, it not halo, cyano or nitro;

Z is NH, oxygen, sulfur, —N($C_1$–$C_4$ alkyl), —NC(=O)($C_1$–$C_2$ alkyl), NC(=O)O($C_1$–$C_2$ alkyl) or $CR^{13}$ $R^{14}$ wherein $R^{13}$ and $R^{14}$ are independently selected from hydrogen, trifluoromethyl and methyl with the exception that one of $R^{13}$ and $R^{14}$ can be cyano;

or a pharmaceutically acceptable salt of such compound.

\* \* \* \* \*